United States Patent
Wang et al.

(10) Patent No.: US 7,427,627 B2
(45) Date of Patent: Sep. 23, 2008

(54) N-(4-(4-METHYLTHIAZOL-5-YL) PYRIMIDIN-2-YL)-N-PHENYLAMINES AS ANTIPROLIFERATIVE COMPOUNDS

(75) Inventors: Shudong Wang, Angus (GB); Christopher Meades, Dundee (GB); Andrew Osnowski, Cumbernauld (GB); Gavin Wood, Fife (GB); Peter Martin Fischer, Angus (GB)

(73) Assignee: Cyclacel Limited, Dundee (GB)

( * ) Notice: Subject to any disclaimer, the term of this patent is extended or adjusted under 35 U.S.C. 154(b) by 0 days.

(21) Appl. No.: 11/433,312

(22) Filed: May 11, 2006

(65) Prior Publication Data

US 2006/0199830 A1 Sep. 7, 2006

Related U.S. Application Data

(63) Continuation of application No. 10/810,767, filed on Mar. 26, 2004, which is a continuation of application No. PCT/GB02/04383, filed on Sep. 27, 2002.

(30) Foreign Application Priority Data

Sep. 28, 2001 (GB) ................... 0123377.4
Oct. 2, 2001 (GB) ................... 0123629.8

(51) Int. Cl.
*C07D 417/04* (2006.01)
*A61K 31/506* (2006.01)

(52) U.S. Cl. ...................... 514/275; 544/331
(58) Field of Classification Search .............. 544/331; 514/275
See application file for complete search history.

(56) References Cited

U.S. PATENT DOCUMENTS 6,531,479 B2 * 3/2003 Wang et al. ................. 514/275

FOREIGN PATENT DOCUMENTS

| EP | 0233461 B1 | 8/1987 |
| WO | WO-95/09847 A1 | 4/1995 |
| WO | WO-97/19065 A1 | 5/1997 |
| WO | WO 01/72745 | * 10/2001 |
| WO | WO-01/72745 A1 | 10/2001 |

OTHER PUBLICATIONS

Blain et al., Differential Interaction of the Cyclin-dependent kinase (Cdk) Inhibitor p27kip1 with Cyclin A-Cdk2 and Cyclin D2-Cdk4, The Journal of Biological Chemistry, vol. 272, No. 41, pp. 25863-25872, 1997.*
LuValle et al., Cell Cycle Control in Growth Plate Chondrocytes, Frontiers in Bioscience 5, d493-503, May 2001.*
Simone, Oncology: Introduction, Cecil Textbook of Medicine, 20th Edition, vol. 1, pp. 1004-1010, 1996.*
Traxler, Protein Tyrosine Kinase Inhibitors in cancer treatment, Expert Opinion on Therapeutic Patents, 7(6):571-588, 1997.*
Paul, Rolf et al., "Preparation of Substituted N-Phenyl-4-aryl-2-pyrimidinamines as Mediator Release Inhibitors," *J. Med. Chem.*, vol. 36:2716-2725 (1993).
Zimmermann, Jürg et al., "Phenylamino-Pyrimidine (PAP) Derivatives: A New Class of Potent and Selective Inhibitors of Protein Kinase C (PKC)," *Arch. Pharm. Pharm. Med. Chem.*, vol. 329:371-376 (1996).

* cited by examiner

*Primary Examiner*—Deepak Rao
(74) *Attorney, Agent, or Firm*—Lahive & Cockfield, LLP; Cynthia L. Kanik; Cynthia M. Soroos, Esq.

(57) ABSTRACT

The present invention relates to 2-substituted 4-heteroaryl-pyrimidines, their preparation, pharmaceutical compositions containing them and their use as inhibitors of cyclin-dependent kinases (CDKs) and hence their use in the treatment of proliferative disorders such as cancer, leukaemia, psoriasis and the like.

25 Claims, 10 Drawing Sheets

| Compound No. | Structure |
|---|---|
| 1 | 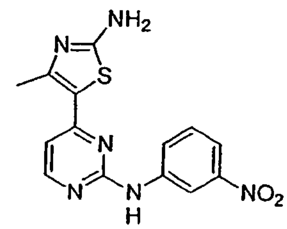 |
| 2 | 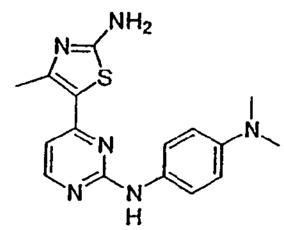 |
| 3 | 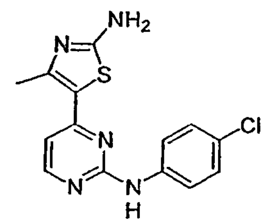 |
| 4 | 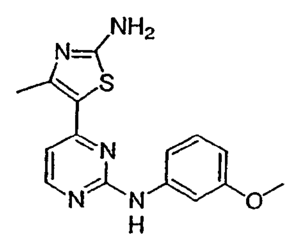 |
| 5 | 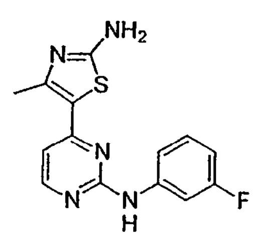 |
| 7 | 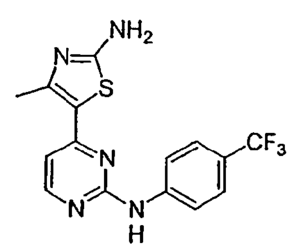 |

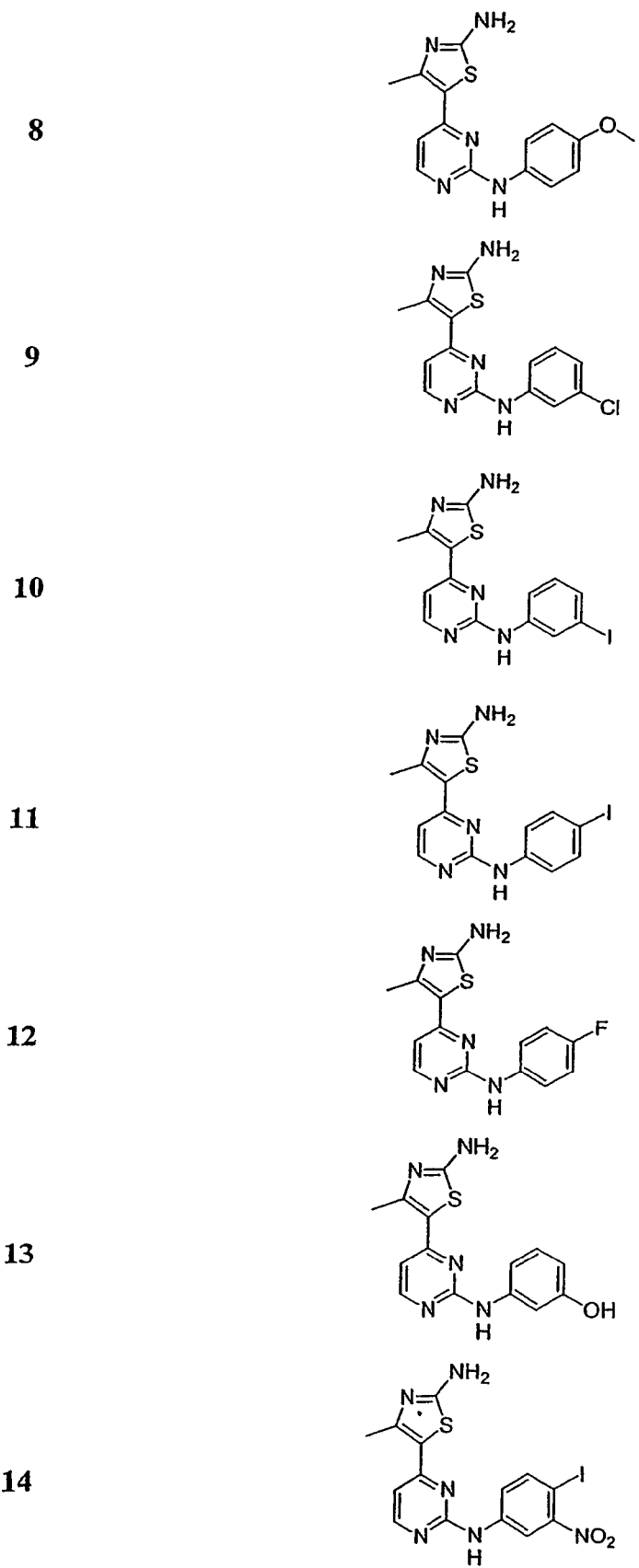

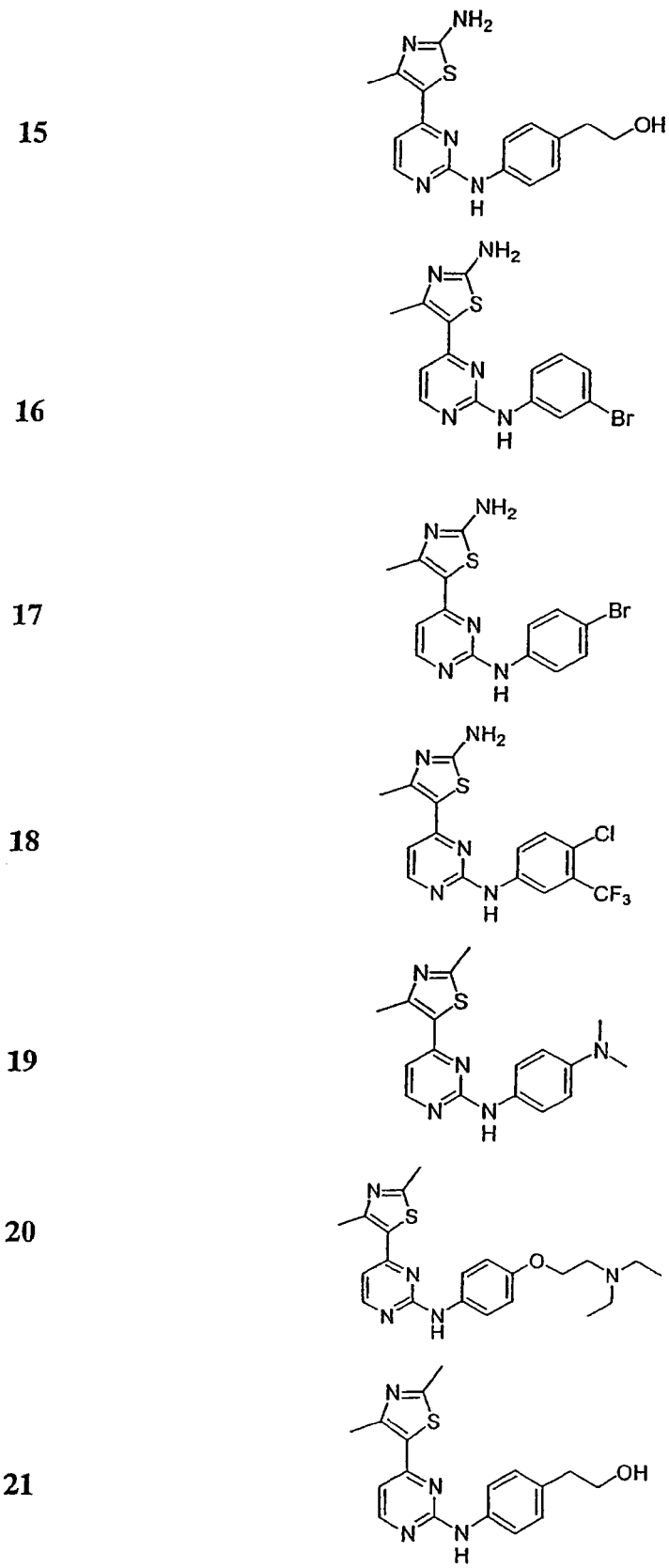

22 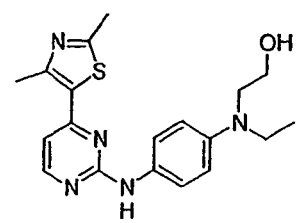
23 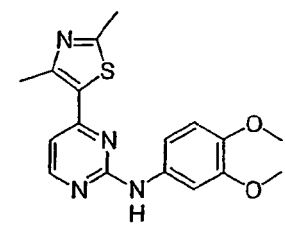
24 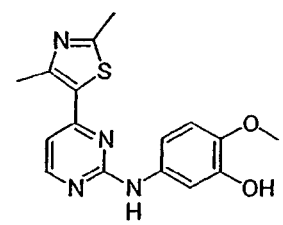
25 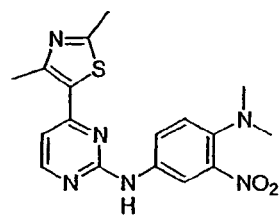
26 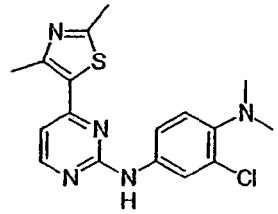
27 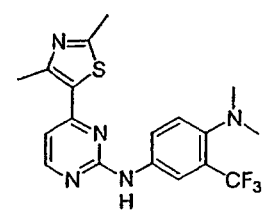
28 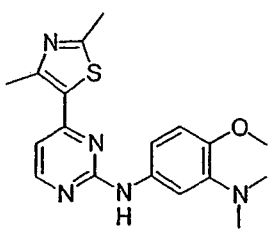

29 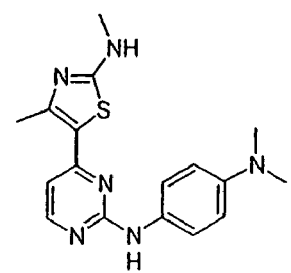
30 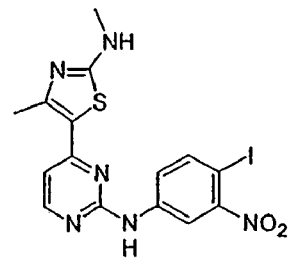
31 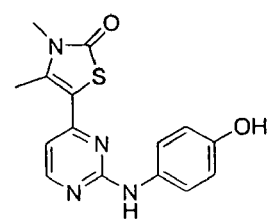
32 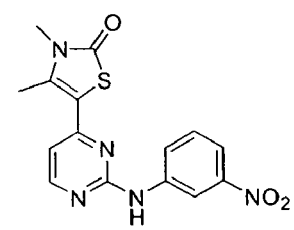
33 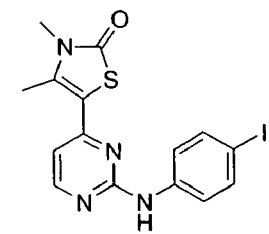
34 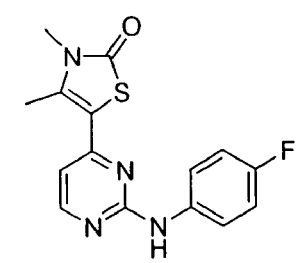

35 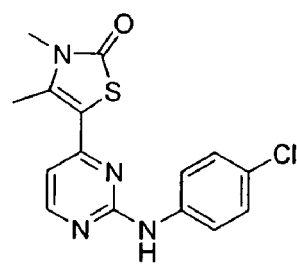
36 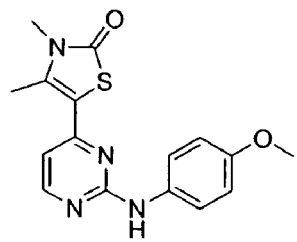
37 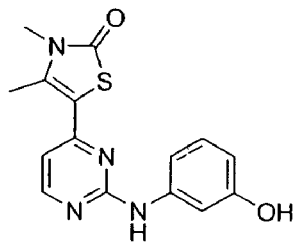
38 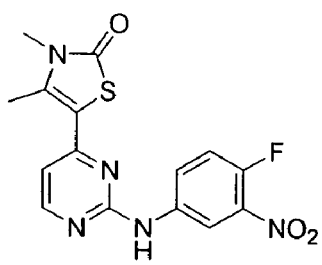
39 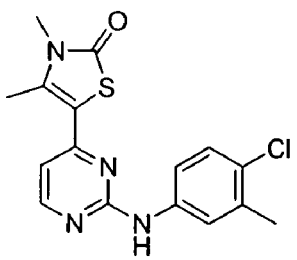
40 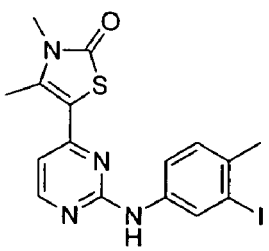

41 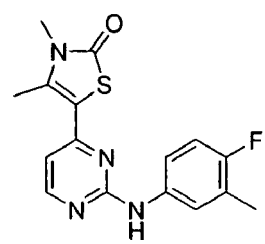
42 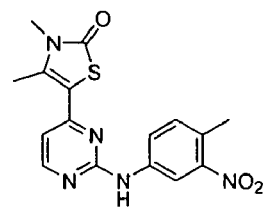
43 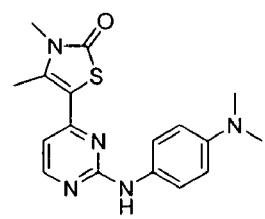
44 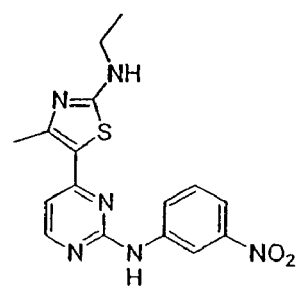
45 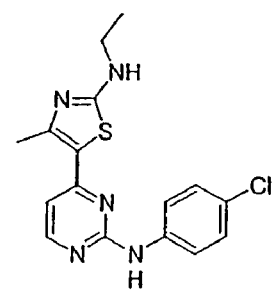
47 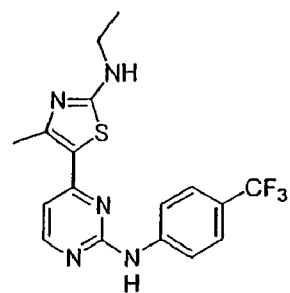

48 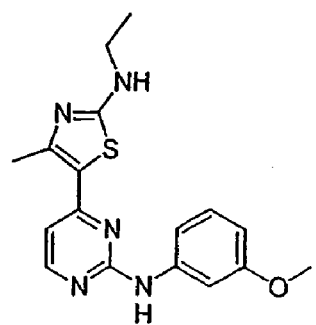
49 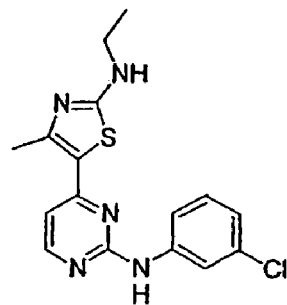
50 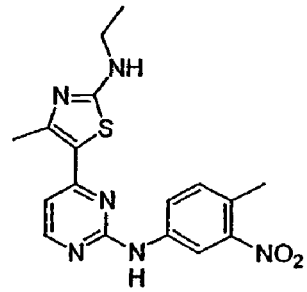
51 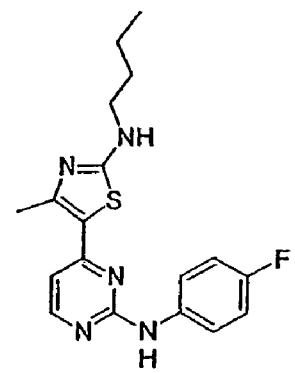
52 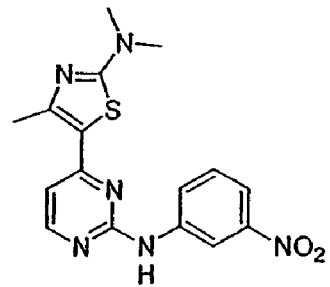

53 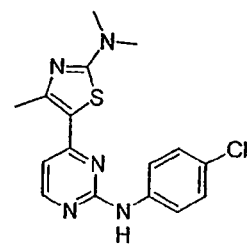
54 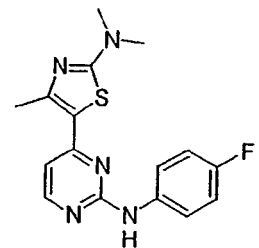
55 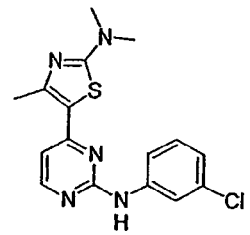
56 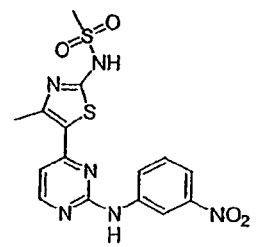
58 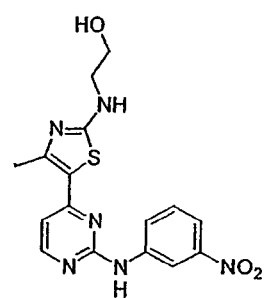
59 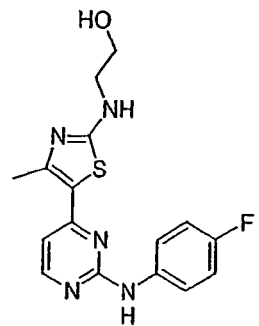

60 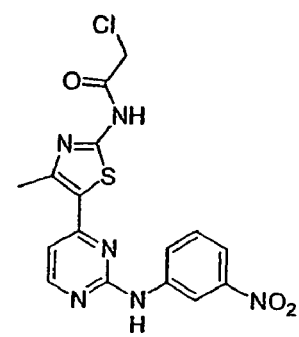
61 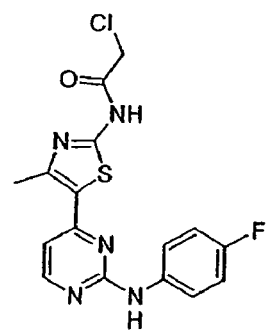
63 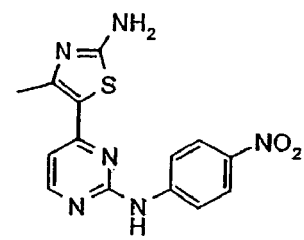
64 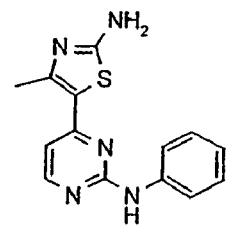
65 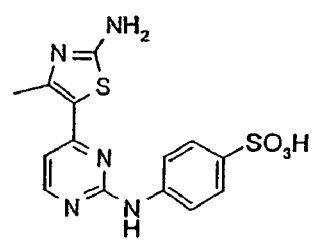
66 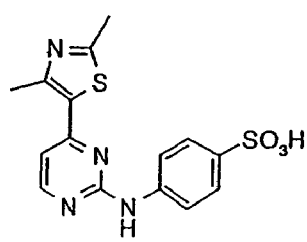

N-(4-(4-METHYLTHIAZOL-5-YL)PYRIMIDIN-2-YL)-N-PHENYLAMINES AS ANTIPROLIFERATIVE COMPOUNDS

RELATED APPLICATIONS

This application is a continuation of U.S. patent application Ser. No. 10/810,767, filed Mar. 26, 2004; which is a continuation of PCT Application No. PCT/GB02/04383, which was filed on Sep. 27, 2002, which claims priority to GB 0123629.8, filed on Oct. 2, 2001, and GB 0123377.4, filed on Sep. 28, 2001. The entire contents of each of these applications are hereby incorporated herein by reference.

FIELD OF THE INVENTION

The present invention relates to 2-substituted 4-heteroaryl-pyrimidines, their preparation, pharmaceutical compositions containing them, and their use in the treatment of proliferative disorders such as cancer, leukemia, psoriasis and the like.

INTRODUCTION AND SUMMARY OF THE PRIOR ART

Certain 4,5,6-substituted-N-(substituted-phenyl)-2-pyrimidineamines having anti-asthmatic properties are disclosed in EP-A-233,461. Certain 4-heteroaryl-N-(3-substituted-phenyl)-2-pyridineamines possessing anti-proliferative properties and inhibiting protein kinases C, epidermal growth factor receptor-associated tyrosine protein kinase, (EGF-R-TPK), as well as CDK1/cyclin B have been disclosed in WO95/09847 wherein the exemplified heteroaryl groups are pyridyl and indolyl.

J. Med. Chem. (1993) Vol. 36, pages 2716-2725, Paul, R. et al: discloses a further class of phenyl amino-pyrimidines possessing anti-inflammatory activity. These compounds include mono-substituted 2-thienyl groups at the 4-position of the pyrimidine ring and dimethyl-3-furyl groups at this position.

PCT/GB01/01423 discloses a broad range of 2-subtituted 4-heteroaryl-pyrimidines which inhibit cyclin-dependent kinases (CDKs) and have applications in the treatment of proliferative disorders such as cancer, leukaemia, psoriasis and the like.

It is an aim of the present invention to provide further N-phenyl-2-pyrimidine anti-proliferative compounds. The compounds of the present invention have surprisingly been found to not to be inhibitors of protein kinase C. As discussed hereinafter, their activity may be demonstrated by inhibition of cell proliferation in cell lines and/or inhibition of cyclin dependent kinase enzymes.

SUMMARY OF THE INVENTION

In a first aspect, the present invention relates to a compound selected from the following:

[4-(2-Amino-4-methyl-thiazol-5-yl)-pyrimidin-2-yl]-(3-nitro-phenyl)-amine [1];
N-[4-(2-Amino-4-methyl-thiazol-5-yl)-pyrimidin-2-yl]-N',N'-dimethyl-benzene-1,4-diamine [2];
[4-(2-Amino-4-methyl-thiazol-5-yl)-pyrimidin-2-yl]-(4-chloro-phenyl)-amine [3];
[4-(2-Amino-4-methyl-thiazol-5-yl)-pyrimidin-2-yl]-(3-methoxy-phenyl)-amine [4];
[4-(2-Amino-4-methyl-thiazol-5-yl)-pyrimidin-2-yl]-(3-fluoro-phenyl)-amine [5];
[4-(2-Amino-4-methyl-thiazol-5-yl)-pyrimidin-2-yl]-(4-trifluoromethyl-phenyl)-amine [7];
[4-(2-Amino-4-methyl-thiazol-5-yl)-pyrimidin-2-yl]-(4-methoxy-phenyl)-amine [8];
[4-(2-Amino-4-methyl-thiazol-5-yl)-pyrimidin-2-yl]-(3-chloro-phenyl)-amine [9];
[4-(2-Amino-4-methyl-thiazol-5-yl)-pyrimidin-2-yl]-(3-iodo-phenyl)-amine [10];
[4-(2-Amino-4-methyl-thiazol-5-yl)-pyrimidin-2-yl]-(4-iodo-phenyl)-amine [11];
[4-(2-Amino-4-methyl-thiazol-5-yl)-pyrimidin-2-yl]-(4-fluoro-phenyl)-amine [12];
3-[4-(2-Amino-4-methyl-thiazol-5-yl)-pyrimidin-2-ylamino]-phenol [13];
[4-(2-Amino-4-methyl-thiazol-5-yl)-pyrimidin-2-yl]-(4-iodo-3-nitro-phenyl)-amine [14];
2-{4-[4-(2-Amino-4-methyl-thiazol-5-yl)-pyrimidin-2-ylamino]-phenyl}-ethanol [15]
[4-(2-Amino-4-methyl-thiazol-5-yl)-pyrimidin-2-yl]-(3-bromo-phenyl)-amine [16];
[4-(2-Amino-4-methyl-thiazol-5-yl)-pyrimidin-2-yl]-(4-bromo-phenyl)-amine [17];
[4-(2-Amino-4-methyl-thiazol-5-yl)-pyrimidin-2-yl]-(4-chloro-3-trifluoromethyl-phenyl)-amine [18];
$N^1$-[4-(2,4-Dimethyl-thiazol-5-yl)-pyrimidin-2-yl]-4-[β-(phenoxy)-triethylamine]-amine [20];
2-{4-[4-(2,4-Dimethyl-thiazol-5-yl)-pyrimidin-2-ylamino]-phenyl}-ethanol [21];
2-({4-[4-(2,4-Dimethyl-thiazol-5-yl)-pyrimidin-2-ylamino]-phenyl}-ethyl-amino)-ethanol [22];
(3,4-Dimethoxy-phenyl)-[4-(2,4-dimethyl-thiazol-5-yl)-pyrimidin-2-yl]-amine [23];
5-[4-(2,4-Dimethyl-thiazol-5-yl)-pyrimidin-2-ylamino]-2-methoxy-phenol [24];
$N^4$-[4-(2,4-Dimethyl-thiazol-5-yl)-pyrimidin-2-yl]-$N^1$,$N^1$-dimethyl-2-nitro-benzene-1,4-diamine [25];
2-[N-(4-N,N-Dimethylamino-3-chlorophenyl)]-4-(2,4-dimethylthiazol-5-yl)-pyrimidineamine [26];
$N^4$-[4-(2,4-Dimethyl-thiazol-5-yl)-pyrimidin-2-yl]-$N^1$,$N^1$-dimethyl-2-trifluoromethyl-benzene-1,4-diamine [27];
$N^1$-[4-(2,4-Dimethyl-thiazol-5-yl)-pyrimidin-2-yl]-4-methoxy-$N^3$,$N^3$-dimethyl-benzene-1,3-diamine [28];
N,N-Dimethyl-N'-[4-(4-methyl-2-methylamino-thiazol-5-yl)-pyrimidin-2-yl]-benzene-1,4-diamine [29];
(4-Iodo-3-nitro-phenyl)-[4-(4-methyl-2-methylamino-thiazol-5-yl)-pyrimidin-2-yl]-amine [30];
5-[2-(4-Hydroxy-phenylamino)-pyrimidin-4-yl]-3,4-dimethyl-3H-thiazol-2-one [31];
3,4-Dimethyl-5-[2-(3-nitro-phenylamino)-pyrimidin-4-yl]-3H-thiazol-2-one [32];
5-[2-(4-Iodo-phenylamino)-pyrimidin-4-yl]-3,4-dimethyl-3H-thiazol-2-one [33];
5-[2-(4-Fluoro-phenylamino)-pyrimidin-4-yl]-3,4-dimethyl-3H-thiazol-2-one [34];
5-[2-(4-Chloro-phenylamino)-pyrimidin-4-yl]-3,4-dimethyl-3H-thiazol-2-one [35];
5-[2-(4-Methoxy-phenylamino)-pyrimidin-4-yl]-3,4-dimethyl-3H-thiazol-2-one [36];
5-[2-(3-Hydroxy-phenylamino)-pyrimidin-4-yl]-3,4-dimethyl-3H-thiazol-2-one [37];
5-[2-(4-Fluoro-3-nitro-phenylamino)-pyrimidin-4-yl]-3,4-dimethyl-3H-thiazol-2-one [38];
5-[2-(4-Chloro-3-methyl-phenylamino)-pyrimidin-4-yl]-3,4-dimethyl-3H-thiazol-2-one [39];
5-[2-(3-Iodo-4-methyl-phenylamino)-pyrimidin-4-yl]-3,4-dimethyl-3H-thiazol-2-one [40];

5-[2-(4-Fluoro-3-methyl-phenylamino)-pyrimidin-4-yl]-3,4-dimethyl-3H-thiazol-2-one [41];
3,4-Dimethyl-5-[2-(4-methyl-3-nitro-phenylamino)-pyrimidin-4-yl]-3H-thiazol-2-one [42];
5-[2-(4-Dimethylamino-phenylamino)-pyrimidin-4-yl]-3,4-dimethyl-3H-thiazol-2-one [43];
[4-(2-Ethylamino-4-methyl-thiazol-5-yl)-pyrimidin-2-yl]-(3-nitro-phenyl)-amine [44];
(4-Chloro-phenyl)-[4-(2-ethylamino-4-methyl-thiazol-5-yl)-pyrimidin-2-yl]-amine [45];
[4-(2-Ethylamino-4-methyl-thiazol-5-yl)-pyrimidin-2-yl]-(4-trifluoromethyl-phenyl)-amine [47];
[4-(2-Ethylamino-4-methyl-thiazol-5-yl)-pyrimidin-2-yl]-(3-methoxy-phenyl)-amine [48];
(3-Chloro-phenyl)-[4-(2-ethylamino-4-methyl-thiazol-5-yl)-pyrimidin-2-yl]-amine [49];
[4-(2-Ethylamino-4-methyl-thiazol-5-yl)-pyrimidin-2-yl]-(4-methyl-3-nitro-phenyl)-amine [50];
[4-(2-Butylamino-4-methyl-thiazol-5-yl)-pyrimidin-2-yl]-(4-fluoro-phenyl)-amine [51];
[4-(2-Dimethylamino-4-methyl-thiazol-5-yl)-pyrimidin-2-yl]-(3-nitro-phenyl)-amine [52];
(4-Chloro-phenyl)-[4-(2-dimethylamino-4-methyl-thiazol-5-yl)-pyrimidin-2-yl]-amine [53];
[4-(2-Dimethylamino-4-methyl-thiazol-5-yl)-pyrimidin-2-yl]-(4-fluoro-phenyl)-amine [54];
(3-Chloro-phenyl)-[4-(2-dimethylamino-4-methyl-thiazol-5-yl)-pyrimidin-2-yl]-amine [55];
N-{4-Methyl-5-[2-(3-nitro-phenylamino)-pyrimidin-4-yl]-thiazol-2-yl}-methanesulfonamide [56];
2-{4-Methyl-5-[2-(3-nitro-phenylamino)-pyrimidin-4-yl]-thiazol-2-ylamino}-ethanol [58];
2-{5-[2-(4-Fluoro-phenylamino)-pyrimidin-4-yl]-4-methyl-thiazol-2-ylamino}-ethanol [59];
2-Chloro-N-{4-methyl-5-[2-(3-nitro-phenylamino)-pyrimidin-4-yl]-thiazol-2-yl}-acetamide [60];
2-Chloro-N-{5-[2-(4-fluoro-phenylamino)-pyrimidin-4-yl]-4-methyl-thiazol-2-yl}-acetamide [61];
[4-(2-Amino-4-methyl-thiazol-5-yl)-pyrimidin-2-yl]-(4-nitro-phenyl)-amine [63];
[4-(2-Amino-4-methyl-thiazol-5-yl)-pyrimidin-2-yl]-(phenyl)-amine [64];
4-[4-(2-Amino-4-methyl-thiazol-5-yl)-pyrimidin-2-yl]-benzenesulfonic acid [65]; and
4-[4-(2,4-Dimethyl-thiazol-5-yl)-pyrimidin-2-ylamino]-benzenesulfonic acid [66].

In a second aspect, the invention relates to a compound selected from the following:
[4-(2-Amino-4-methyl-thiazol-5-yl)-pyrimidin-2-yl]-(3-nitro-phenyl)-amine [1];
[4-(2-Amino-4-methyl-thiazol-5-yl)-pyrimidin-2-yl]-(4-trifluoromethyl-phenyl)-amine [7];
[4-(2-Amino-4-methyl-thiazol-5-yl)-pyrimidin-2-yl]-(4-methoxy-phenyl)-amine [8];
[4-(2-Amino-4-methyl-thiazol-5-yl)-pyrimidin-2-yl]-(3-chloro-phenyl)-amine [9];
[4-(2-Amino-4-methyl-thiazol-5-yl)-pyrimidin-2-yl]-(3-iodo-phenyl)-amine [10];
[4-(2-Amino-4-methyl-thiazol-5-yl)-pyrimidin-2-yl]-(4-iodo-phenyl)-amine [11];
[4-(2-Amino-4-methyl-thiazol-5-yl)-pyrimidin-2-yl]-(4-fluoro-phenyl)-amine [12];
[4-(2-Amino-4-methyl-thiazol-5-yl)-pyrimidin-2-yl]-(3-bromo-phenyl)-amine [16];
[4-(2-Amino-4-methyl-thiazol-5-yl)-pyrimidin-2-yl]-(4-bromo-phenyl)-amine [17];
N-{4-Methyl-5-[2-(3-nitro-phenylamino)-pyrimidin-4-yl]-thiazol-2-yl}-methanesulfonamide [56];
2-{4-Methyl-5-[2-(3-nitro-phenylamino)-pyrimidin-4-yl]-thiazol-2-ylamino}-ethanol [58];
2-{5-[2-(4-Fluoro-phenylamino)-pyrimidin-4-yl]-4-methyl-thiazol-2-ylamino}-ethanol [59];
2-Chloro-N-{4-methyl-5-[2-(3-nitro-phenylamino)-pyrimidin-4-yl]-thiazol-2-yl}-acetamide [60];
2-Chloro-N-{5-[2-(4-fluoro-phenylamino)-pyrimidin-4-yl]-4-methyl-thiazol-2-yl}-acetamide [61];
[4-(2-Amino-4-methyl-thiazol-5-yl)-pyrimidin-2-yl]-(4-nitro-phenyl)-amine [63];
[4-(2-Amino-4-methyl-thiazol-5-yl)-pyrimidin-2-yl]-(phenyl)-amine [64];
4-[4-(2-Amino-4-methyl-thiazol-5-yl)-pyrimidin-2-yl]-benzenesulfonic acid [65]; and
4-[4-(2,4-Dimethyl-thiazol-5-yl)-pyrimidin-2-ylamino]-benzenesulfonic acid [66].

In a third aspect, the invention provides a pharmaceutical composition comprising one or more of said compounds together with a pharmaceutically acceptable carrier, excipient or diluent.

In a fourth aspect, the invention relates to the use of one or more of said compounds in the treatment of a proliferative disorder.

DETAILED DESCRIPTION

Figure 1:
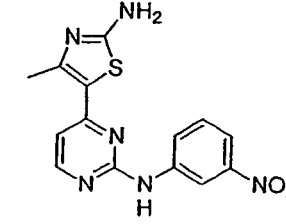
FIG. 1 shows the chemical structures of compounds [1]-[66].
Figure 1:
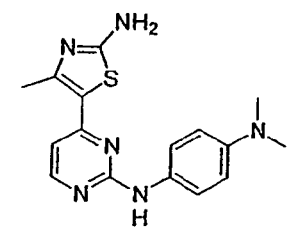
Figure 1:
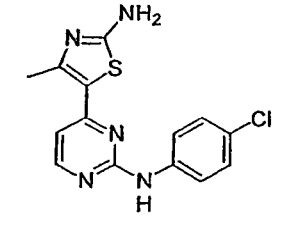
Figure 1:
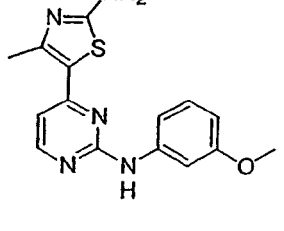
Figure 1:
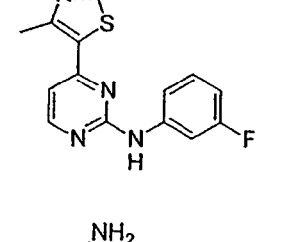
Figure 1:

In a preferred embodiment of the first aspect of the invention, the compound is selected from the following:
[4-(2-Amino-4-methyl-thiazol-5-yl)-pyrimidin-2-yl]-(3-nitro-phenyl)-amine [1];
[4-(2-Amino-4-methyl-thiazol-5-yl)-pyrimidin-2-yl]-(3-chloro-phenyl)-amine [9];
[4-(2-Amino-4-methyl-thiazol-5-yl)-pyrimidin-2-yl]-(3-iodo-phenyl)-amine [10];
3-[4-(2-Amino-4-methyl-thiazol-5-yl)-pyrimidin-2-ylamino]-phenol [13];
[4-(2-Amino-4-methyl-thiazol-5-yl)-pyrimidin-2-yl]-(4-iodo-3-nitro-phenyl)-amine [14];
[4-(2-Amino-4-methyl-thiazol-5-yl)-pyrimidin-2-yl]-(3-bromo-phenyl)-amine [16];
(3,4-Dimethoxy-phenyl)-[4-(2,4-dimethyl-thiazol-5-yl)-pyrimidin-2-yl]-amine [23];
$N^4$-[4-(2,4-Dimethyl-thiazol-5-yl)-pyrimidin-2-yl]-$N^1$,$N^1$-dimethyl-2-nitro-benzene-1,4-diamine [25];
2-[N-(4-N,N-Dimethylamino-3-chlorophenyl)]-4-(2,4-dimethylthiazol-5-yl)-pyrimidineamine [26];
N,N-Dimethyl-N'-[4-(4-methyl-2-methylamino-thiazol-5-yl)-pyrimidin-2-yl]-benzene-1,4-diamine [29];
5-[2-(4-Hydroxy-phenylamino)-pyrimidin-4-yl]-3,4-dimethyl-3H-thiazol-2-one [31];
3,4-Dimethyl-5-[2-(3-nitro-phenylamino)-pyrimidin-4-yl]-3H-thiazol-2-one [32];
5-[2-(4-Fluoro-phenylamino)-pyrimidin-4-yl]-3,4-dimethyl-3H-thiazol-2-one [34];
3,4-Dimethyl-5-[2-(4-methyl-3-nitro-phenylamino)-pyrimidin-4-yl]-3H-thiazol-2-one [42];
N-{4-Methyl-5-[2-(3-nitro-phenylamino)-pyrimidin-4-yl]-thiazol-2-yl}-methanesulfonamide [56];
2-{4-Methyl-5-[2-(3-nitro-phenylamino)-pyrimidin-4-yl]-thiazol-2-ylamino}-ethanol [58];

2-Chloro-N-{4-methyl-5-[2-(3-nitro-phenylamino)-pyrimidin-4-yl]-thiazol-2-yl}-acetamide [60]; and
2-Chloro-N-{5-[2-(4-fluoro-phenylamino)-pyrimidin-4-yl]-4-methyl-thiazol-2-yl}-acetamide [61].

In a more preferred embodiment of the first aspect of the invention, the compound is selected from the following:
[4-(2-Amino-4-methyl-thiazol-5-yl)-pyrimidin-2-yl]-(3-nitro-phenyl)-amine [1];
[4-(2-Amino-4-methyl-thiazol-5-yl)-pyrimidin-2-yl]-(3-chloro-phenyl)-amine [9];
[4-(2-Amino-4-methyl-thiazol-5-yl)-pyrimidin-2-yl]-(3-iodo-phenyl)-amine [10];
[4-(2-Amino-4-methyl-thiazol-5-yl)-pyrimidin-2-yl]-(3-bromo-phenyl)-amine [16];
$N^4$-[4-(2,4-Dimethyl-thiazol-5-yl)-pyrimidin-2-yl]-$N^1,N^1$-dimethyl-2-nitro-benzene-1,4-diamine [25];
2-[N-(4-N,N-Dimethylamino-3-chlorophenyl)]-4-(2,4-dimethylthiazol-5-yl)-pyrimidineamine [26];
5-[2-(4-Hydroxy-phenylamino)-pyrimidin-4-yl]-3,4-dimethyl-3H-thiazol-2-one [31];
3,4-Dimethyl-5-[2-(3-nitro-phenylamino)-pyrimidin-4-yl]-3H-thiazol-2-one [32];
N-{4-Methyl-5-[2-(3-nitro-phenylamino)-pyrimidin-4-yl]-thiazol-2-yl}-methanesulfonamide [56]; and
2-{4-Methyl-5-[2-(3-nitro-phenylamino)-pyrimidin-4-yl]-thiazol-2-ylamino}-ethanol [58].

In an alternative preferred embodiment of the first aspect of the invention, the compound is selected from the following:
3-[4-(2-Amino-4-methyl-thiazol-5-yl)-pyrimidin-2-ylamino]-phenol [13];
[4-(2-Amino-4-methyl-thiazol-5-yl)-pyrimidin-2-yl]-(4-iodo-3-nitro-phenyl)-amine [14];
(3,4-Dimethoxy-phenyl)-[4-(2,4-dimethyl-thiazol-5-yl)-pyrimidin-2-yl]-amine [23];
N,N-Dimethyl-N'-[4-(4-methyl-2-methylamino-thiazol-5-yl)-pyrimidin-2-yl]-benzene-1,4-diamine [29];
5-[2-(4-Fluoro-phenylamino)-pyrimidin-4-yl]-3,4-dimethyl-3H-thiazol-2-one [34];
3,4-Dimethyl-5-[2-(4-methyl-3-nitro-phenylamino)-pyrimidin-4-yl]-3H-thiazol-2-one [42];
2-Chloro-N-{4-methyl-5-[2-(3-nitro-phenylamino)-pyrimidin-4-yl]-thiazol-2-yl}-acetamide [60]; and
2-Chloro-N-{5-[2-(4-fluoro-phenylamino)-pyrimidin-4-yl]-4-methyl-thiazol-2-yl}-acetamide [61].

In a particularly preferred embodiment of the first aspect of the invention, the compound is 3,4-Dimethyl-5-[2-(3-nitro-phenylamino)-pyrimidin-4-yl]-3H-thiazol-2-one [32] or 2-{4-Methyl-5-[2-(3-nitro-phenylamino)-pyrimidin-4-yl]-thiazol-2-ylamino}-ethanol [58].

In a preferred embodiment of the second aspect of the invention, the compound is selected from the following:
[4-(2-Amino-4-methyl-thiazol-5-yl)-pyrimidin-2-yl]-(3-nitro-phenyl)-amine [1];
[4-(2-Amino-4-methyl-thiazol-5-yl)-pyrimidin-2-yl]-(3-chloro-phenyl)-amine [9];
[4-(2-Amino-4-methyl-thiazol-5-yl)-pyrimidin-2-yl]-(3-iodo-phenyl)-amine [10];
[4-(2-Amino-4-methyl-thiazol-5-yl)-pyrimidin-2-yl]-(3-bromo-phenyl)-amine [16];
N-{4-Methyl-5-[2-(3-nitro-phenylamino)-pyrimidin-4-yl]-thiazol-2-yl}-methanesulfonamide [56];
2-{4-Methyl-5-[2-(3-nitro-phenylamino)-pyrimidin-4-yl]-thiazol-2-ylamino}-ethanol [58];
2-Chloro-N-{4-methyl-5-[2-(3-nitro-phenylamino)-pyrimidin-4-yl]-thiazol-2-yl}-acetamide [60]; and
2-Chloro-N-{5-[2-(4-fluoro-phenylamino)-pyrimidin-4-yl]-4-methyl-thiazol-2-yl}-acetamide [61].

In a more preferred embodiment of the second aspect of the invention, the compound is selected from the following:
[4-(2-Amino-4-methyl-thiazol-5-yl)-pyrimidin-2-yl]-(3-nitro-phenyl)-amine [1];
[4-(2-Amino-4-methyl-thiazol-5-yl)-pyrimidin-2-yl]-(3-chloro-phenyl)-amine [9];
[4-(2-Amino-4-methyl-thiazol-5-yl)-pyrimidin-2-yl]-(3-iodo-phenyl)-amine [10];
[4-(2-Amino-4-methyl-thiazol-5-yl)-pyrimidin-2-yl]-(3-bromo-phenyl)-amine [16];
N-{4-Methyl-5-[2-(3-nitro-phenylamino)-pyrimidin-4-yl]-thiazol-2-yl}-methanesulfonamide [56]; and
2-{4-Methyl-5-[2-(3-nitro-phenylamino)-pyrimidin-4-yl]-thiazol-2-ylamino}-ethanol [58].

In an even more preferred embodiment of the second aspect of the invention, the compound is selected from the following:
[4-(2-amino-4-methyl-thiazol-5-yl)-pyrimidin-2-yl]-(3-nitro-phenyl)-amine [1];
N-{4-Methyl-5-[2-(3-nitro-phenylamino)-pyrimidin-4-yl]-thiazol-2-yl}-methanesulfonamide [56]; and
2-{4-Methyl-5-[2-(3-nitro-phenylamino)-pyrimidin-4-yl]-thiazol-2-ylamino}-ethanol [58].

In an alternative preferred embodiment of the second aspect of the invention, the compound is selected from the following:
2-Chloro-N-{4-methyl-5-[2-(3-nitro-phenylamino)-pyrimidin-4-yl]-thiazol-2-yl}-acetamide [60]; and
2-Chloro-N-{5-[2-(4-fluoro-phenylamino)-pyrimidin-4-yl]-4-methyl-thiazol-2-yl}-acetamide [61].

In one particularly preferred embodiment of the second aspect of the invention, the is [4-(2-Amino-4-methyl-thiazol-5-yl)-pyrimidin-2-yl]-(3-nitro-phenyl)-amine [1].

The compounds of the invention have been found to possess anti-proliferative activity and are therefore believed to be of use in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29, Saos-2, HeLa or MCF-7, or by showing inhibition of a CDK enzyme (such as CDK2 or CDK4) in an appropriate assay. These assays, including methods for their performance, are described in more detail in the accompanying Examples. Using such cell line and enzymes assays it may be determined whether a compound is anti-proliferative in the context of the present invention.

Without wishing to be bound by theory, the compounds of the present invention are believed to exert their anti-proliferative effect in a non-protein kinase C (PKC) dependent manner. Many of the compounds inhibit cyclin-dependent kinase enzymes (CDKs) that have been shown to be involved in cell cycle control. These CDKs include CDK2 and CDK4 and particularly their respective interactions with cyclin E and cyclin D1. These compounds of the present invention are further believed to be advantageous in being selective for CDK enzymes implicated in proliferative diseases. By the term "selective" it is meant that although possibly having some inhibitory effect on another enzyme (such as PKC), the compound is preferentially effective against an enzyme implicated in proliferative diseases.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

One embodiment of the present invention therefore relates to the use of one or more compounds of the invention in the treatment of proliferative disorders. Preferably, the proliferative disorder is a cancer or leukaemia. The term proliferative disorder is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, antiparasitic disorders such as malaria, emphysema and alopecia. In these disorders, the compounds of the present invention may induce apoptosis or maintain stasis within the desired cells as required.

In a particularly preferred embodiment, the invention relates to the use of one or more compounds of the invention in the treatment of a CDK dependent or sensitive disorder. CDK dependent disorders are associated with an above normal level of activity of one or more CDK enzymes. Such disorders preferably associated with an abnormal level of activity of CDK2 and/or CDK4. A CDK sensitive disorder is a disorder in which an aberration in the CDK level is not the primary cause, but is downstream of the primary metabolic aberration. In such scenarios, CDK2 and/or CDK4 can be said to be part of the sensitive metabolic pathway and CDK inhibitors may therefore be active in treating such disorders. Such disorders are preferably cancer or leukaemic disorders.

A third aspect of the present invention relates to the use of one or more compounds of the invention, and pharmaceutically acceptable salts thereof, in the manufacture of a medicament for use in the treatment of a proliferative disease.

The term "proliferative disorder" has been previously discussed and the same definition applies to the second aspect of the invention.

In a particularly preferred embodiment, the one or more compounds of the invention are administered in combination with one or more other anticancer agents. In such cases, the compounds of the invention may be administered consecutively, simultaneously or sequentially with the one or more other anticancer agents.

As used herein the phrase "manufacture of a medicament" includes the use of a compound of the invention directly as the medicament in addition to its use in a screening programme for further anti-proliferative agents or in any stage of the manufacture of such a medicament.

The compounds of the present invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

In all aspects of the present invention previously discussed, the invention includes, where appropriate all enantiomers and tautomers of compounds of invention. The man skilled in the art will recognise compounds that possess an optical properties (one or more chiral carbon atoms) or tautomeric characteristics. The corresponding enantiomers and/or tautomers may be isolated/prepared by methods known in the art.

The invention furthermore relates to the compounds of, or of use, in the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

The invention further includes the compounds of, or of use, in the present invention in prodrug form. Such prodrugs are generally compounds of the invention wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

The present invention also encompasses pharmaceutical compositions comprising the compounds of the invention. In this regard, and in particular for human therapy, even though the compounds of the present invention (including their pharmaceutically acceptable salts, esters and pharmaceutically acceptable solvates) can be administered alone, they will generally be administered in admixture with a pharmaceutical carrier, excipient or diluent selected with regard to the intended route of administration and standard pharmaceutical practice.

Thus, the present invention also relates to pharmaceutical compositions comprising one or more compounds of the invention or pharmaceutically acceptable salts or esters thereof, together with at least one pharmaceutically acceptable excipient, diluent or carrier.

By way of example, in the pharmaceutical compositions of the present invention, the compounds of the invention may be admixed with any suitable binder(s), lubricant(s), suspending agent(s), coating agent(s), and/or solubilising agent(s). Examples of such suitable excipients for the various different forms of pharmaceutical compositions described herein may be found in the "Handbook of Pharmaceutical Excipients, $2^{nd}$ Edition, (1994), Edited by A Wade and P J Weller.

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

A person of ordinary skill in the art can easily determine an appropriate dose of one of the instant compositions to administer to a subject without undue experimentation. Typically, a physician will determine the actual dosage which will be most suitable for an individual patient and it will vary with the age, weight and response of the particular patient. The dosages disclosed herein are exemplary of the average case. There can of course be individual instances where higher or lower dosage ranges are merited, and such are within the scope of this invention.

In an exemplary embodiment, one or more doses of 10 to 150 mg/day will be administered to the patient for the treatment of malignancy.

The pharmaceutical compositions of the invention may further comprise one or more additional anticancer agents, for example, existing anticancer drugs available on the market.

Anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

Suitable anti-proliferative agents that may be used in combination with at least one compound of the present invention include: DNA damaging agents, anti-metabolites, anti-tumour antibiotics, natural products and their analogues, dihydrofolate reductase inhibitors, pyrimidine analogues, purine analogues, cyclin-dependent kinase inhibitors, thymidylate synthase inhibitors, DNA intercalators, DNA cleavers, topoisomerase inhibitors, anthracyclines, vinca drugs, mitomycins, bleomycins, cytotoxic nucleosides, pteridine drugs, diynenes, podophyllotoxins, platinum containing drugs, differentiation inducers, and taxanes. Particularly useful members of those classes include, for example, methotrexate, methopterin, dichloromethotrexate, 5-fluorouracil, 6-mercaptopurine, tri-substituted purines such as olomoucine, roscovitine, bohemine and purvalanol, flavopiridol, staurosporin, cytosine arabinoside, melphalan, leurosine, actinomycin, daunorubicin, doxorubicin, mitomycin D, mitomycin A, carninomycin, aminopterin, tallysomycin, podophyllotoxin (and derivatives thereof), etoposide, cisplatin, carboplatinum, vinblastine, vincristine, vindesin, paclitaxel, docetaxel, taxotere retinoic acid, butyric acid, acetyl spermidine, tamoxifen, irinotecan and camptothecin. Most preferably the drug moiety is selected from methotrexate, podophyllotoxin (and derivatives thereof), etoposide, camptothecin, paclitaxel, doxorubicin, roscovitine and bohemine.

By way of example, the compounds of the invention can be synthesised, by the route shown below in Scheme 1:

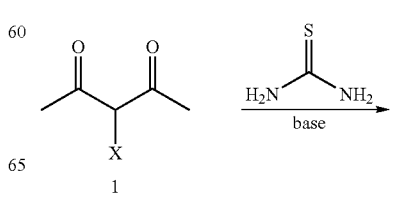

Scheme 1

-continued

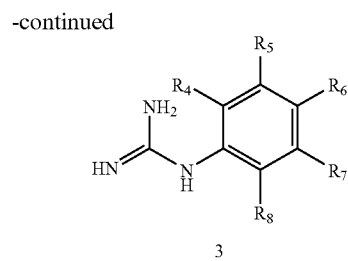

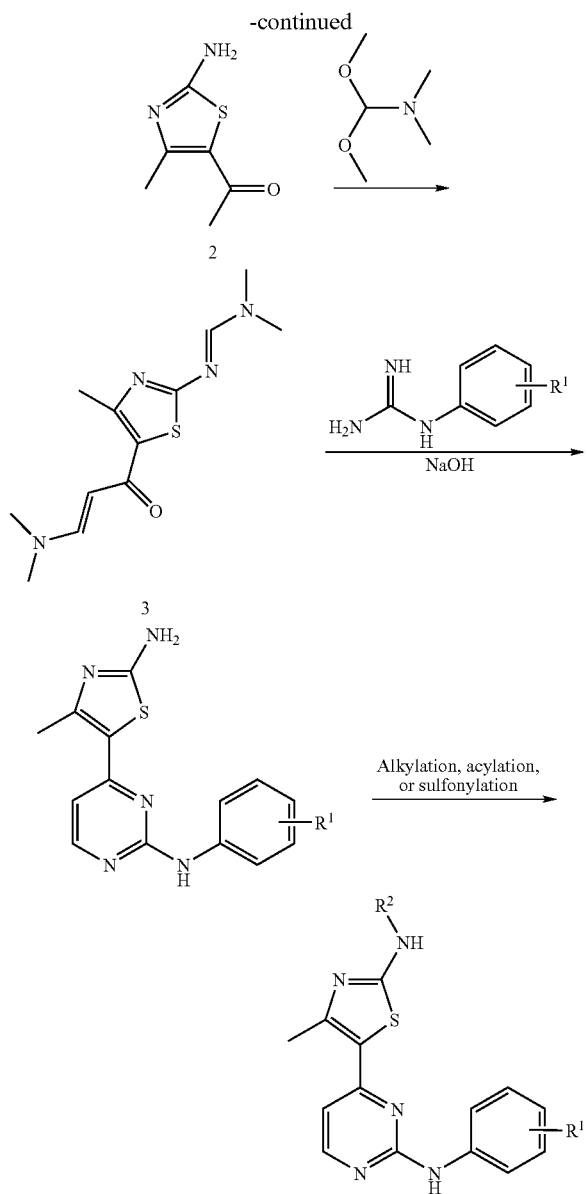

As illustrated, acrylate 2 is obtained from heterocyclic methyl ketone 1 by condensation with dimethylformamide dimethylacetal.

Guanidine 3 (Scheme 2) can be elaborated by a number of methods known in the art. For the purposes of this invention, the most useful route is amination of cyanamide 4 with anilines 5.

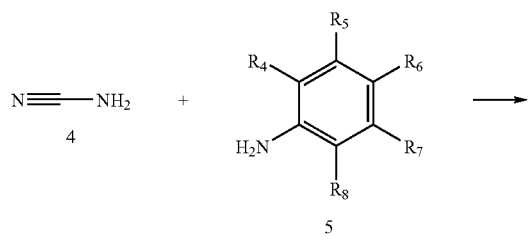

The present invention is further described by way of example and with reference to FIG. 1 which shows the chemical structures of the compounds of the present invention.

EXAMPLES

Abbreviations

DE MALDI-TOF MS, delayed extraction matrix assisted laser desorption ionisation time-of-flight mass spectrometry; DMF, N,N-dimethylformamide; NMR, nuclear magnetic resonance spectroscopy; RP-HPLC, reversed-phase high performance liquid chromatography; r.t., room temperature; PE, petroleum ether (40-60° C. boiling fraction); DMSO, dimethylsulfoxide.

General

NMR spectra were recorded using a Varian INOVA 500 MHz instrument. Chemical shifts are reported in ppm (δ) from tetramethylsilane. Silica gel 60 (0.040-0.063 mm) was used for column chromatography.

Example 1

[4-(2-Amino-4-methyl-thiazol-5-yl)-pyrimidin-2-yl]-(3-nitro-phenyl)-amine [1]

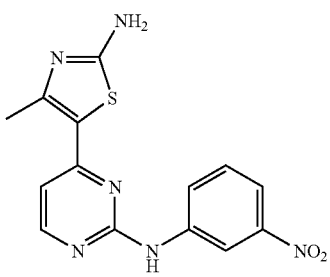

A mixture of thiourea (5.18 g, 0.068 mol) in dry MeOH (20 mL) was stirred and cooled on an ice bath. Pyridine (2 mL) was added, followed by 3-chloro-2,4-pentadione (9.15 g, 0.068 mol) dropwise. After completion of the addition the reaction mixture was allowed to warm to r. t. and stirring was continued for 4 h. The precipitates were filtered and washed with EtOAc to afford white solid 1-(2-amino-4-methyl-thiazol-5-yl)-ethanone.

A solution of this material (3.35 g, 0.021 mol) in N,N-dimethylformamide dimethylacetal (10 mL) was refluxed under $N_2$ for 4-6 h. The reaction mixture was evaporated to dryness. EtOAc was added to the residue and the precipitates were collected by filtration and were washed with EtOAc/PE (5:1, v/v) to afford N'-[5-(3-dimethylamino-acryloyl)-4-methyl-thiazol-2-yl]-N,N-dimethyl-formamidine as an orange solid (50-79%). ¹H-NMR (CDCl₃) δ: 2.64 (s, 3H, CH₃), 3.08 (s, 6H, CH₃), 3.11 (s, 6H, CH₃), 5.35 (d, 1H, J=12.2 Hz, CH), 7.67 (d, 1H, J=12.2 Hz, CH), 8.23 (s, 1H, N=CH). DE MALDI-TOF MS: [M+H]⁺=267.49 (C₁₂H₁₈N₆OS requires 266.36).

A mixture of this material (2.19 g, 8.2 mmol) and 3-nitrophenyl guanidine nitrate (2.00 g 8.2 mmol) in 2-methoxyethanol (10 mL) was treated with NaOH (0.33 g). After refluxing under N₂ for 20 h the reaction mixture was concentrated and purified by silica-gel chromatography using EtOAc/PE (7:1) to elute the title compound as a light-yellow solid (1.95 g, 72%), which was then recrystallised from EtOAc/MeOH. ¹H-NMR (DMSO-d₆) δ: 3.13 (s, 3H, CH₃), 7.02 (d, 1H, J=5.5 Hz, Py-H), 7.59 (m, 4H, Ph-H and NH₂), 7.82 (m, 1H, Ph-H), 8.16 (m, 1H, Ph-H), 8.44 (d, 1H, J=5.5 Hz, Py-H), 8.86 (br. s, 1H, NH).

Example 2

The following compounds were prepared in a manner similar to that described in Example 1 above:

N-[4-(2-Amino-4-methyl-thiazol-5-yl)-pyrimidin-2-yl]-N¹,N¹-dimethyl-benzene-1,4-diamine [2]

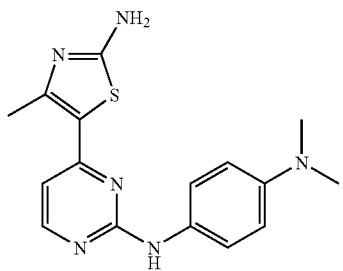

Yellow solid; anal. RP-HPLC: t_R=9.83 min (0-60% MeCN in 0.1% aq CF₃COOH over 20 min, 1 mL/min, purity >95%). ¹H-NMR (CD₃OD) δ: 2.58 (s, 3H, CH₃), 3.28 (s, 6H, CH₃), 7.08 (d, 1H, J=5.5 Hz, pyrimidinyl-H), 7.56 (m, 2H, Ph-H), 7.89 (m, 2H, Ph-H), 8.45 (d, 1H, J=5.5 Hz, pyrimidinyl-H). MS (DE MALDI-TOF) m/z=326.0 [M+H]⁺ (C₁₆H₁₈N₆S requires 326.4).

[4-(2-Amino-4-methyl-thiazol-5-yl)-pyrimidin-2-yl]-(4-chloro-phenyl)-amine [3]

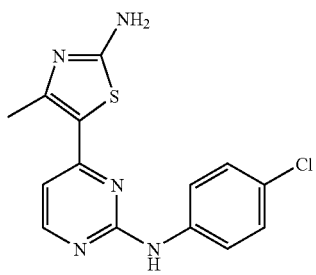

Brown solid; ¹H-NMR (DMSO-d₆) δ: 2.42 (s, 3H, CH₃), 6.88 (d, 1H, J=5.0 Hz, pyrimidinyl-H), 7.28 (m, 2H, Ph-H), 7.51 (br. s, 2H, NH₂), 7.77 (m, 2H, Ph-H), 8.32 (d, 1H, J=5.1 Hz, pyrimidinyl-H), 9.56 (br. s, 1H, NH). MS (DE MALDI-TOF) m/z=318.4 [M+H]⁺ (C₁₄H₁₂ClN₅S requires 317.8).

[4-(2-Amino-4-methyl-thiazol-5-yl)-pyrimidin-2-yl]-(3-methoxy-phenyl)-amine [4]

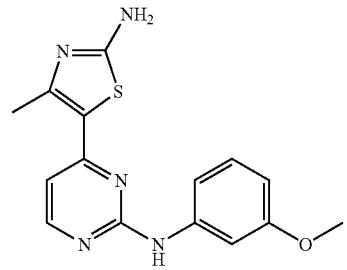

Light yellow solid; ¹H-NMR (DMSO-d₆) δ: 2.41 (s, 3H, CH₃), 3.72 (s, 3H, CH₃), 6.50 (m, 1H, Ph-H), 6.88 (d, 1H, J=5.5 Hz, pyrimidinyl-H), 7.14 (t, 1H, J=8.0 Hz, Ph-H), 7.30 (m, 1H, Ph-H), 7.47 (m, 1H, pyrimidinyl-H), 7.48 (br. s, 2H, NH₂), 8.31 (d, 1H, J=5.5 Hz, pyrimidinyl-H), 9.41 (br. s, 1H, NH).

[4-(2-Amino-4-methyl-thiazol-5-yl)-pyrimidin-2-yl]-(3-fluoro-phenyl)-amine [5]

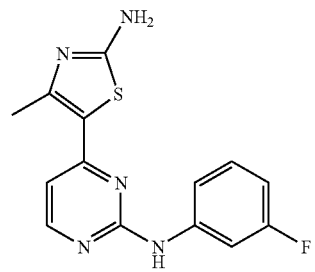

Grey solid; ¹H-NMR (DMSO-d₆) δ: 2.43 (s, 3H, CH₃), 6.71 (m, 1H, Ph-H), 6.92 (d, 1H, J=5.5 Hz, pyrimidinyl-H), 7.27 (m, 1H, Ph-H), 7.44 (m, 1H, Ph-H), 7.557 (br. s, 2H, NH₂), 7.84 (m, 1H, Ph-H), 8.35 (d, 1H, J=5.5 Hz, pyrimidinyl-H), 9.69 (sr. 1H, NH).

[4-(2-Amino-4-methyl-thiazol-5-yl)-pyrimidin-2-yl]-(4-trifluoromethyl-phenyl)-amine [7]

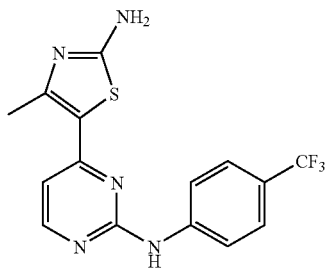

Brown solid; ¹H-NMR (DMSO-d₆) δ: 2.44 (s, 3H, CH₃), 6.96 (d, 1H, J=5.0 Hz, pyrimidinyl-H), 7.53 (br. s, 2H, NH₂), 7.60 (d, 2H, J=9.0 Hz, Ph-H), 7.97 (d, 2H, J=8.5 Hz, Ph-H), 8.38 (d, 1H, J=5.0 Hz, pyrimidinyl-H), 9.86 (br. s, H, NH). MS (DE MALDI-TOF) m/z=352.0 [M+H]+ ($C_{15}H_{12}F_3N_5S$ requires 351.4).

[4-(2-Amino-4-methyl-thiazol-5-yl)-pyrimidin-2-yl]-(4-methoxy-phenyl)-amine [8]

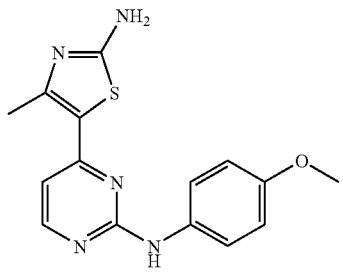

Brown solid; $^1$H-NMR (DMSO-$d_6$) δ: 2.41 (s, 3H, CH$_3$), 3.71 (s, 3H, CH$_3$), 6.80 (d 1H, J=5.5 Hz, pyrimidinyl-H), 6.84 (m, 2H, Ph-H), 7.44 (br. s, 1H, NH), 7.63 (m, 2H, Ph-H), 8.26 (d, 1H, J=5.5 Hz, pyrimidinyl-H), and 9.20 (br. s, H, NH). MS (DE MALDI-TOF) m/z=312.9 [M+H]+ ($C_{15}H_{15}N_5OS$ requires 313.4).

[4-(2-Amino-4-methyl-thiazol-5-yl)-pyrimidin-2-yl]-(3-chloro-phenyl)-amine [9]

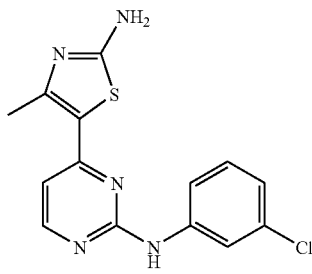

Brown solid; $^1$H-NMR (DMSO-$d_6$) δ: 2.43 (s, 3H, CH$_3$), 6.91 (d, 1H, J=5.5 Hz, pyrimidinyl-H), 6.94 (m, 1H, Ph-H), 7.26 (m, 1H, Ph-H), 7.55 (br. s 2H, NH$_2$), 7.64 (m, 1H, Ph-H), 8.02 (s, 1H, Ph-H), 8.34 (d, 1H, J=5.5 Hz, pyrimidinyl-H), 9.64 (br. s, 1H, NH).

[4-(2-Amino-4-methyl-thiazol-5-yl)-pyrimidin-2-yl]-(3-iodo-phenyl)-amine [10]

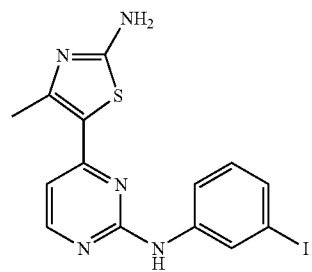

Dark solid; $^1$H-NMR (DMSO-$d_6$) δ: 2.44 (s, 3H, CH$_3$), 6.90 (d, 1H, J=5.5 Hz, pyrimidinyl-H), 7.04 (t, 1H, J=7.5 Hz, Ph-H), 7.25 (m, 1H, Ph-H), 7.51 (br. s, 2H, NH$_2$), 7.65 (m, 1H, Ph-H), 8.26 (s, 1H, Ph-H), 8.34 (d, 1H, J=5.5 Hz, pyrimidinyl-H), 9.64 (br. s, 1H, NH). MS (DE MALDI-TOF) m/z=408.9 ($C_{14}H_{12}IN_5S$ requires 409.3).

[4-(2-Amino-4-methyl-thiazol-5-yl)-pyrimidin-2-yl]-(4-iodo-phenyl)-amine [11]

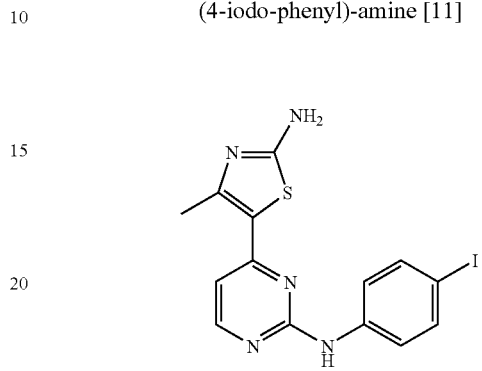

Yellow solid; $^1$H-NMR (DMSO-$d_6$) δ: 2.48 (s, 3H, CH$_3$), 7.04 (d, 1H, J=5.5 Hz, pyrimidinyl-H), 7.59 (s, 2H, NH$_2$), 8.01 (m, 2H, Ph-H), 8.17 (m, 2H, Ph-H), 8.43 (d, 1H, J=5.5 Hz, pyrimidinyl-H), 10.27 (br. s, 1H, NH).

[4-(2-Amino-4-methyl-thiazol-5-yl)-pyrimidin-2-yl]-(4-fluoro-phenyl)-amine [12]

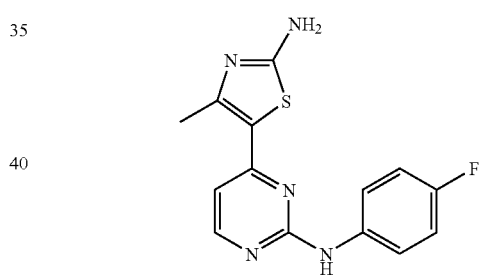

Grey solid; $^1$H-NMR (DMSO-$d_6$) δ: 2.42 (s, 3H, CH$_3$), 6.86 (d, 1H, J=5.5 Hz, pyrimidinyl-H), 7.08 (m, 2H, Ph-H), 7.48 (br. s, 2H, NH$_2$), 7.74 (m, 2H, Ph-H), 8.30 (d, 1H, J=5.5 Hz, pyrimidinyl-H), 8.50, 9.42 (br. s 1H, NH). MS (DE MALDI-TOF) m/z=299.6 [M+H]+ ($C_{14}H_{12}FN_5S$ requires 301.3).

3-[4-(2-Amino-4-methyl-thiazol-5-yl)-pyrimidin-2-ylamino]-phenol [13]

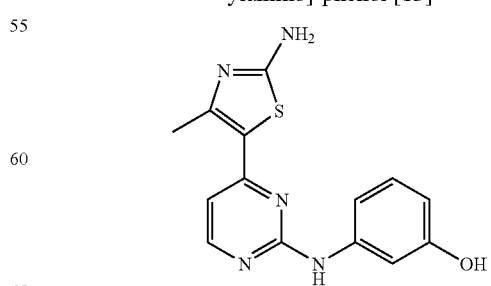

Dark-brown solid; $^1$H-NMR (DMSO-$D_6$) δ: 2.41 (s, 3H, CH$_3$), 6.34 (m, 1H, Ph-H), 6.84 (d, 1H, J=5.5 Hz, pyrimidinyl-H), 7.01 (m, 1H, Ph-H), 7.19 (s, 1H, Ph-H), 7.23 (m, 1H, Ph-H), 7.48 (br. s, 2H, NH₂), 8.29 (d, 1H, J=5.5 Hz, pyrimidinyl-H), 9.26 (br. s, 2H, NH & OH).

[4-(2-Amino-4-methyl-thiazol-5-yl)-pyrimidin-2-yl]-(4-iodo-3-nitro-phenyl)-amine [14]

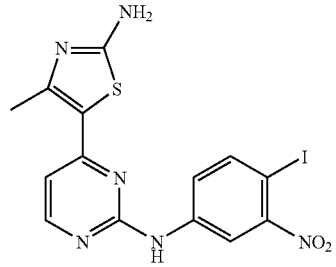

Dark solid; anal. RP-HPLC: $t_R$=15.5 min (0-60% MeCN in 0.1% aq CF₃COOH over 20 min, 1 mL/min, purity >95%). ¹H-NMR (DMSO-d₆) δ: 2.48 (s, 3H, CH₃), 6.92 (d, 1H, J=5.5 Hz, pyrimidinyl-H), 7.37 (m, 1H, Ph-H), 7.82 (m, 1H, Ph-H), 8.19 (m, 1H, Ph-H), 8.36 (d, 1H, J=5.5 Hz, pyrimidinyl-H), 8.68 (br. s, 2H, NH₂), 9.86 (br. s, 1H, NH).

2-{4-[4-(2-Amino-4-methyl-thiazol-5-yl)-pyrimidin-2-ylamino]-phenyl}-ethanol [15]

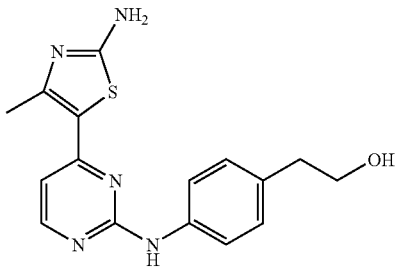

Light yellow solid; anal. RP-HPLC: $t_R$=10.9 min (0-60% MeCN in 0.1% aq CF₃COOH over 20 min, 1 mL/min, purity >95%). ¹H-NMR (DMSO-d₆) δ: 2.85 (s, 3H, CH₃), 3.04 (t, 2H, J=7.32 Hz, CH₂), 3.94 (t, 2H, J=7.32 Hz, CH₂), 7.35 (d, 1H, J=5.5 Hz, pyrimidinyl-H), 7.50 (d, 2H, J=8.5 Hz, Ph-H), 7.96 (d, 2H, J=8.5 Hz, Ph-H), 8.76 (d, 1H, J=5.5 Hz, pyrimidinyl-H), 8.68 (br. s, 2H, NH₂), 9.12 (br. s, 2H, NH & OH).

[4-(2-Amino-4-methyl-thiazol-5-yl)-pyrimidin-2-yl]-(3-bromo-phenyl)-amine [16]

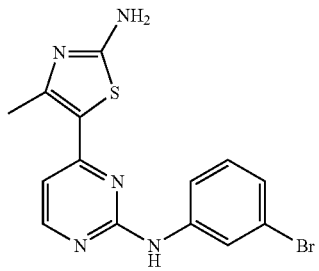

Yellow solid; ¹H-NMR (DMSO-d₆) δ: 2.44 (s, 3H, CH₃), 6.91 (d, 1H, J=5.4 Hz, Py-H), 7.08 (m, 1H, Ph-H), 7.20 (m, 1H, Ph-H), 7.53 (m, 1H, Ph-H), 7.68 (m, 1H, Ph-H), 8.15 (br. s, 2H, NH₂), 8.35 (d, 1H, J=5.4 Hz, pyrimidinyl-H), 9.62 (br. s 1H, NH). MS (DE MALDI-TOF) m/z=362.2 (C₁₄H₁₂BrN₅S requires 362.3).

[4-(2-Amino-4-methyl-thiazol-5-yl)-pyrimidin-2-yl]-(4-bromo-phenyl)-amine [17]

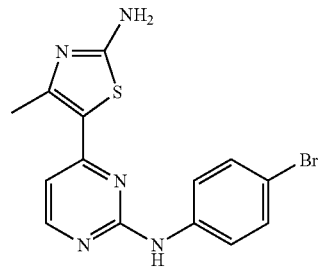

Brown solid; ¹H-NMR (DMSO-d₆) δ: 2.43 (s, 3H, CH₃), 6.89 (d, 1H, J=5.5 Hz, pyrimidinyl-H), 7.42 (m, 2H, Ph-H), 7.47 (br. s, 2H, NH₂), 7.73 (m, 2H, Ph-H), 8.33 (d, 1H, J=5.5 Hz, pyrimidinyl-H), 9.57 (br. s, 1H, NH). MS (DE MALDI-TOF) m/z=362.2 (C₁₄H₁₂BrN₅S requires 362.3).

[4-(2-Amino-4-methyl-thiazol-5-yl)-pyrimidin-2-yl]-(4-chloro-3-trifluoromethyl-phenyl)-amine [18]

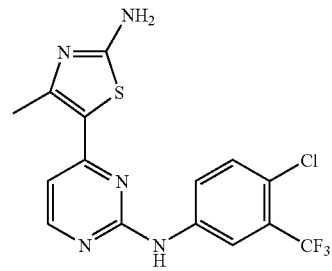

Brown solid; ¹H-NMR (DMSO-d₆) δ: 2.43 (s, 3H, CH₃), 6.96 (d, 1H, J=5.6 Hz, pyrimidinyl-H), 7.76 (m, 2H, Ph-H/NH), 8.00 (m, 1H, Ph-H), 8.38 (m, 2H, Py-H/Ph-H), 9.89 (br. s, 1H, NH). MS (DE MALDI-TOF) m/z=388.8 [M+H]⁺ (C₁₅H₁₁ClF₃N₅S requires 385.8).

Example 3

N-[4-(2,4-Dimethyl-thiazol-5-yl)-pyrimidin-2-yl]-N',N'-dimethyl-benzene-1,4-diamine [19]

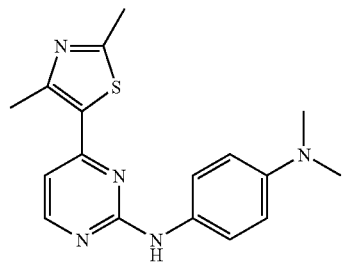

A solution of 1-(2,4-dimethyl-thiazol-5-yl)-ethanone (10 g, 0.06 mol) in of N,N-dimethylformamide dimethylacetal (10 mL) was refluxed under N₂. After 18 h, the reaction mixture was evaporated to dryness in vacuo. The resulting solid material was crystallised from a minimum amount of isopropyl ether/CH₂Cl₂ to afford 9.94 g 3-dimethylamino-1-(2,4-dimethyl-thiazol-5-yl)-propenone as a brown powder (79%). ¹H-NMR (CDCl₃) δ: 2.66 (s, 6H, CH₃), 2.70 (s, 6H, CH₃), 5.37 (d, 1H, J=12.2 Hz, CH), 7.66 (d, 1H, J=12.2 Hz, CH).

To a solution of this compound (0.21 g, 1.0 mmol) and N-(4-dimethylamino-phenyl)-guanidine nitrate (50 mg) (prepared from N,N-dimethyl-benzene-1,4-diamine and cyanamide) in 2-methoxyethanol (3 mL) was added NaOH (80 mg). The reaction mixture was refluxed for 8 h. The solvent was evaporated in vacuo and the residue was purified by SiO$_2$ flash chromatography (EtOAc) to afford 2-[N-(4-N,N-dimethylaminophenyl)]-4-(2,4-dimethylthiazol-5-yl)-pyrimidineamine [19] as a yellow solid (26 mg, 79%). RP-HPLC: t$_R$=11.2 min (0-60% MeCN in 0.1% aq CF$_3$COOH over 20 min, 1 mL/min, purity >95%). $^1$H-NMR (DMSO-d$_6$) δ: 2.60 (s, 3H, CH$_3$), 2.62 (s, 3H, CH$_3$), 2.82 (s, 6H, CH$_3$), 6.70 (d, 2H, J=8.8 Hz, Ph-H), 6.95 (d, 1H, J=5.3 Hz, pyrimidinyl-H), 7.53 (d, 2H, J=8.9 Hz, Ph-H), 8.40 (d, 1H, J=5.3 Hz, pyrimidinyl-H), 9.26 (br. s, 1H, NH). MS (ESI$^+$) m/z=326.2 [M+H]$^+$ (C$_{17}$H$_{19}$N$_5$S requires 325.4).

Example 4

The following compounds were prepared in a manner analogous to that described in Example 3 above:

N$^1$-[4-(2,4-Dimethyl-thiazol-5-yl)-pyrimidin-2-yl]-4-[β-(phenoxy)-triethylamine]-amine [20]

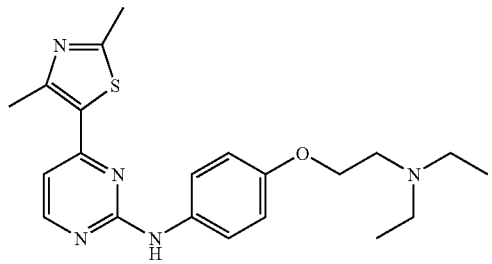

Buff-coloured solid; $^1$H-NMR (CD$_3$OD) δ: 1.11 (t, 6H, J=7.3 Hz, CH$_3$), 2.66 (s, 3H, CH$_3$), 2.68 (s, 3H, CH$_3$), 2.70 (q, 4H, J=7.1 Hz, CH$_2$), 2.93 (t, 2H, J=5.6 Hz, CH$_2$), 4.10 (t, 2H, J=5.9 Hz, CH$_2$), 6.91 (d, 2H, J=9.3 Hz, Ph-H), 6.99 (d, 1H, J=5.4 Hz, pyrimidinyl-H), 7.56 (d, 2H, J=9.3 Hz, Ph-H), 8.37 (d, 1H, J=5.1 Hz, pyrimidinyl-H). MS (DE MALDI-TOF) m/z=397.2 [M+H]$^+$ (C$_{21}$H$_{27}$N$_5$OS requires 397.5).

2-{4-[4-(2,4-Dimethyl-thiazol-5-yl)-pyrimidin-2-ylamino]-phenyl}-ethanol [21]

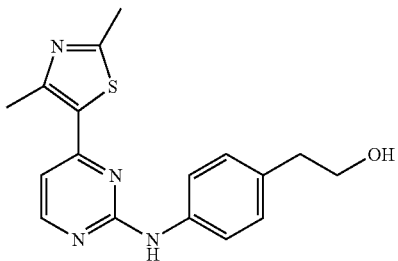

Light yellow solid; anal. RP-HPLC: t$_R$=13.1 min (0-60% MeCN in 0.1% aq CF$_3$COOH over 20 min, 1 mL/min, purity >95%). $^1$H-NMR (DMSO-d$_6$) δ: 2.89 (s, 3H, CH$_3$), 3.07 (m, 2H, CH$_2$), 3.98 (t, 2H, J=7.5 Hz, CH$_2$), 7.46 (d, 1H, J=5.5 Hz, pyrimidinyl-H), 7.55 (d, 2H, J=8.5 Hz, Ph-H), 8.06 (d, 2H, J=8.5 Hz, Ph-H), 8.90 (d, 1H, J=5.5 Hz, pyrimidinyl-H). MS (ESI$^+$) m/z=326.7 (C$_{17}$H$_{18}$N$_4$OS requires 326.4).

2-({4-[4-(2,4-Dimethyl-thiazol-5-yl)-pyrimidin-2-ylamino]-phenyl}-ethyl-amino)-ethanol [22]

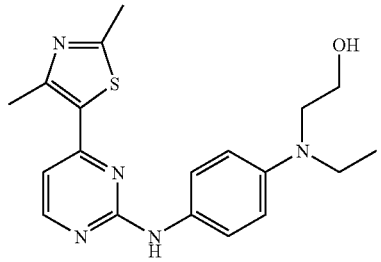

Yellow solid; $^1$H-NMR (CDCl$_3$) δ: 1.08 (t, 3H, J=7.1 Hz, CH$_3$), 2.61 (s, 3H, CH$_3$), 2.64 (s, 3H, CH$_3$), 3.34 (q, 2H, J=7.1 Hz, CH$_2$), 3.46 (br. s, 1H, OH), 6.36 (t, 2H, J=5.9 Hz, CH$_2$), 6.70 (t, 2H, J=5.4 Hz, CH$_2$), 6.76 (d, 2H, J=9.0 Hz, Ph-H), 6.79 (d, 1H, J=5.1 Hz, pyrimidinyl-H), 6.84 (br. s, 1H, NH), 7.39 (d, 2H, J=9.0 Hz, Ph-H), 8.30 (d, 1H, J=5.1 Hz, pyrimidinyl-H).

(3,4-Dimethoxy-phenyl)-[4-(2,4-dimethyl-thiazol-5-yl)-pyrimidin-2-yl]-amine [23]

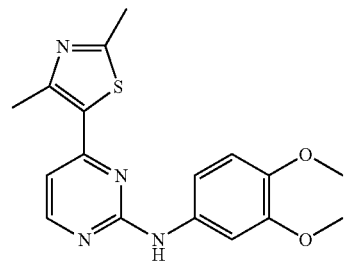

Brown solid; $^1$H-NMR (CDCl$_3$) δ: 2.69 (s, 3H, CH$_3$), 2.70 (s, 3H, CH$_3$), 3.89 (s, 3H, CH$_3$), 3.95 (s, 3H, CH$_3$), 6.87 (d, 1H, J=8.5 Hz, Ph-H), 6.92 (d, 1H, J=5.1 Hz, pyrimidinyl-H), 7.04 (dd, 1H, J=8.5, 2.2 Hz, Ph-H), 7.14 (br. s, 1H, NH), 7.36 (m, 1H, Ph-H), 8.38 (d, 1H, J=5.4 Hz, pyrimidinyl-H).

5-[4-(2,4-Dimethyl-thiazol-5-yl)-pyrimidin-2-ylamino]-2-methoxy-phenol [24]

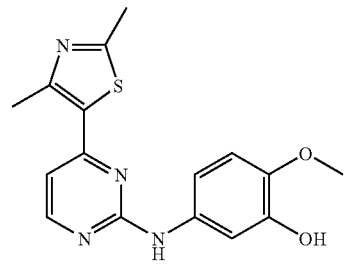

Yellow solid; $^1$H-NMR (DMSO-d$_6$) δ: 2.61 (s, 3H, CH$_3$), 2.63 (s, 3H, CH$_3$), 3.72 (s, 3H, CH$_3$), 6.83 (d, 1H, J=8.8 Hz, Ph-H), 6.99 (d, 1H, J=5.4 Hz, pyrimidinyl-H), 7.15-7.19 (m, 2H, Ph-H, NH), 8.44 (d, 1H, J=5.6 Hz, pyrimidinyl-H), 8.82 (br. s, 1H, OH), 9.34 (d, 1H, J=1.5 Hz, Ph-H).

Example 5

N[4]-[4-(2,4-Dimethyl-thiazol-5-yl)-pyrimidin-2-yl-]-N[1],N[1]-dimethyl-2-nitro-benzene-1,4-diamine [25]

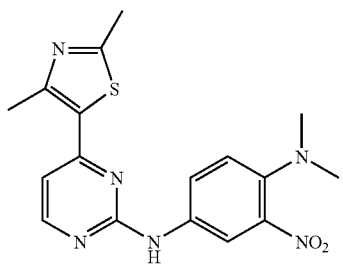

HNO$_3$ (69% aq, 24 µL, 0.36 mmol) was added dropwise to Ac$_2$O (1 mL) at room temperature, keeping the internal temperature below 25° C. The mixture was stirred at room temperature for 15 min before cooling to −5° C. in an ice-MeOH bath. Compound N-[4-(2,4-dimethyl-thiazol-5-yl)-pyrimidin-2-yl]-N',N'-dimethyl-benzene-1,4-diamine (50 mg, 0.15 mmol) was slurried in Ac$_2$O (1 mL) and added dropwise to the cooled solution of acetyl nitrate. The mixture was stirred with cooling for 1 h then a further 2 h at room temperature. The mixture was poured into ice-water (20 mL) and the pH was adjusted to 7-8 by addition of saturated aq NaHCO$_3$ solution. The mixture was extracted with EtOAc. The combined organics were washed with brine, dried on MgSO$_4$, and filtered. The solvent was evaporated in vacuo to give a dark solid, which was purified by flash chromatography, eluted with heptane/EtOAc to afford 32 mg of the title compound as a pale reddish solid. RP-HPLC: t$_R$=12.7 min (10-70% MeCN in 0.1% aq CF$_3$COOH over 20 min, 1 mL/min, purity >95%). $^1$H-NMR (DMSO-d$_6$): δ 2.62 (s, 3H, CH$_3$), 2.64 (s, 3H, CH$_3$), 2.74 (s, 6H, CH$_3$), 7.09 (d, 1H, J=5.1 Hz, pyrimidinyl-H), 7.23 (d, 1H, J=8.8 Hz, Ph-H), 7.77 (dd, 1H, J=8.7, 2.7 Hz, Ph-H), 8.39 (d, 1H, J=2.7 Hz), 8.51 (d, 1H, J=5.1 Hz, pyrimidinyl-H), 9.81 (br. s, 1H, NH).

In an alternative preparation: 4-Fluoro-3-nitro-aniline (20 g, 128 mmol) was dissolved in EtOH (300 mL) and dimethylamine (5.6 M solution in EtOH, 360 mL, 2.02 mol) was added in a steady stream. After refluxing for 18 h, the reaction mixture was cooled and 100 mL water was added. EtOH was removed by evaporation and the residue was extracted with Et$_2$O (3×100 mL). The combined organics were washed with brine, filtered, and the solvent was evaporated to afford 22.8 g of 4-(dimethylamino)-3-nitroaniline as a black oil. This was dissolved in EtOH (80 mL) and HNO$_3$ (69% aq, 18.5 mL, 22.1 mmol) added dropwise followed by cyanamide (50% wt in water, 37 mL, 476 mmol). The mixture was heated at reflux for 18 h. Once cooled, the mixture was poured into Et$_2$I (1 L). The ethereal supernatant was decanted and the residue was treated with propan-2-ol, followed by Et$_2$O to give 19.0 g of the corresponding guanidine nitrate as a tan solid. This was stirred with K$_2$CO$_3$ (15.04 g, 108.8 mmol) in 2-methoxyethanol (250 mL) for 10 min before adding 3-dimethylamino-1-(2,4-dimethylthiazol-5-yl)-propenone (9.53 g, 45.33 mmol). The mixture was heated at 125° C. for 18 h. The reaction mixture was concentrated and diluted with EtOAc, filtered through a pad of silica and evaporated to give a dark oil, which was purified by chromatography, using EtOAc to elute the title product as a reddish solid. Recrystallisation from toluene yielded 7.3 g pure title compounds.

Example 6

2-[N-(4-N,N-Dimethylamino-3-chlorophenyl)]-4-(2,4-dimethylthiazol-5-yl)-pyrimidineamine [26]

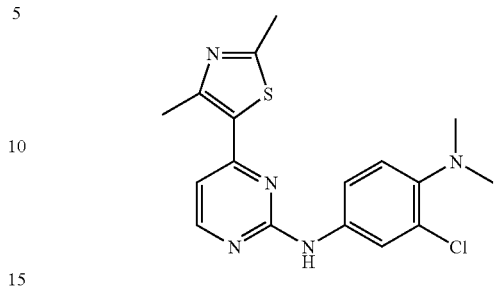

A solution of 3-chloro-4-fluoronitrobenzene (3.0 g, 17.1 mmol), dimethylamine hydrochloride (1.53 g, 18.8 mmol) and K$_2$CO$_3$ (4.96 g, 35.9 mmol) in Me$_2$SO (20 mL) was heated in a sealed tube at 105° C. for 18 h. On cooling the reaction mixture was poured into water (200 mL) and extracted with EtOAc. The combined organics were washed with brine, dried on MgSO$_4$, filtered, and evaporated to give 3.47 g of 3-chloro-4-(dimethylamino) nitrobenzene as a yellow solid. An aliquot of this (3.4 g, 16.95 mmol) was dissolved in 20 mL of EtOH/AcOH (1:1, v/v) with warming. Iron powder (−325 mesh, 9.5 g, 170 mmol) was added in small portions. The mixture was then heated on a steam bath for 30 min. The mixture was cooled, filtered through a pad of celite and the filtrate was evaporated to give 3.33 g of 3-chloro-4-(dimethylamino)aniline as a dark solid. A solution of this compound in EtOH (10 mL) was treated with HNO$_3$ (69% aq, 2.6 mL, 40.6 mmol) dropwise, followed by cyanamide (50% solution in water, 5.3 mL, 67.78 mmol). After heating for 18 h at reflux the reaction mixture was cooled to room temperature, poured into Et$_2$O (100 ml) and basified with NaOH solution (2 N, 100 mL). The ethereal layer was separated. The aqueous phase was extracted with Et$_2$O. The combined organic phases were washed with brine, dried on MgSO$_4$, filtered, and evaporated to give a black oil, which solidified on standing to afford 1.6 g of the title compound. RP-HPLC: t$_R$=12.7 min (10-70% MeCN in 0.1% aq CF$_3$COOH over 20 min, 1 mL/min, purity >95%). $^1$H-NMR (CD$_3$OD) δ: 2.68 (s, 3H, CH$_3$), 2.70 (s, 3H, CH$_3$), 2.75 (s, 6H, CH$_3$), 7.05 (d, 1H, J=5.1 Hz), 7.15 (d, 1H, J=8.8 Hz, pyrimidinyl-H), 7.49 (dd, 1H, J=8.8, 2.4 Hz, Ph-H), 7.94 (d, 1H, J=2.4 Hz, Ph-H), 8.43 (d, 1H, J=5.4 Hz, pyimidinyl-H). MS (ESI$^+$) m/z=393 [M+Na] (C$_{17}$H$_{18}$N$_6$O$_2$S requires 370.4).

Example 7

The following compounds were prepared in a manner analogous to that described in Example 6 above:

N[4]-[4-(2,4-Dimethyl-thiazol-5-yl)-pyrimidin-2-yl]-N[1],N[1]-dimethyl-2-trifluoromethyl-benzene-1,4-diamine [27]

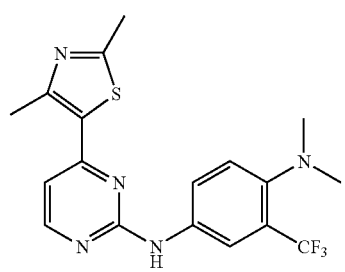

Off-white solid; ¹H-NMR (CDCl₃) δ: 2.62 (s, 3H, CH₃), 2.64 (s, 9H, CH₃), 6.91 (d, 1H, J=5.5 Hz), 7.16 (br. s, 1H, NH), 7.31 (d, 1H, J=8.5 Hz, pyrimidinyl-H), 7.63 (dd, 1H, J=9.0, 2.5 Hz, Ph-H), 7.94 (d, 1H, J=2.5 Hz, Ph-H), 8.36 (d, 1H, J=5.0 Hz, pyrimidinyl-H).

N¹-[4-(2,4-Dimethyl-thiazol-5-yl)-pyrimidin-2-yl]-4-methoxy-N³,N³-dimethyl -benzene-1,3-diamine [28]

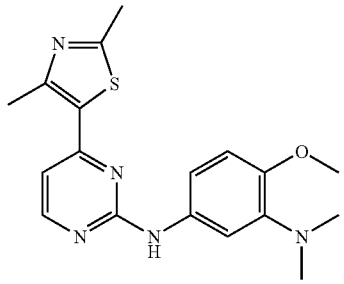

Off-white solid; ¹H-NMR (CDCl₃) δ: 2.58 (s, 3H, CH₃), 2.62 (s, 3H, CH₃), 2.67 (s, 6H, CH₃), 3.74 (s, 3H, CH₃), 6.84 (d, 1H, J=8.5 Hz, pyrimidinyl-H), 6.98 (d, 1H, J=5.0 Hz, pyrimidinyl-H), 7.33 (m, 1H, Ph-H), 8.44 (d, 1H, J=5.0 Hz, pyrimidinyl-H), 9.33 (br. s, 1H, NH).

Example 8

N,N-Dimethyl-N'-[4-(4-methyl-2-methylamino-thiazol-5-yl)-pyrimidin-2-yl]-benzene-1,4-diamine [29]

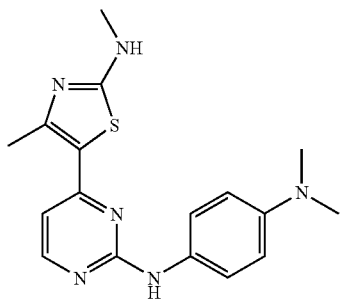

A solution of 3-chloro-2,4-pentanone (2.5 g, 19 mmol) in MeOH (15 mL) was treated with N-methyl-2-thiourea (1.67 g, 19 mmol) and pyridine (15 mL). After stirring at room temperature for 3 h the resulting precipitates were filetered and washed with Et₂O to afford of 1-(4-methyl-2-methylamino-thiazol-5-yl)-ethanone (2.05 g) as a white solid. Without further purification this compound was treated with of N,N-dimethylformamide dimethylacetal (10 mL at 100-110° C. for 22 h. The reaction mixture was concentrated and the precipitate was collected and washed with EtOAc to afford 3-dimethylamino-1-(4-methyl-2-methylaminothiazol-5-yl)-propenone as an orange solid. ¹H-NMR (CDCl₃) δ: 2.55 (s, 3H, CH₃), 2.94 (s, 3H, CH₃), 3.40 (s, 6H, CH₃), 5.29 (d, 1H, J=12.2 Hz, CH), 7.62 (d, 1H, J=12.2 Hz, CH).

The title compounds was then obtained by condensation of 3-dimethylamino-1-(4-methyl-2-methylaminothiazol-5-yl)-propenone and N-(4-dimethylamino-phenyl)-guanidine nitrate as usual. Dark-brown solid; anal. RP-HPLC: t_R=10.2 min (0-60% MeCN in 0.1% aq CF₃COOH over 20 min, 1 mL/min, purity >95%). ¹H-NMR (DMSO-d₆) δ: 2.62 (s, 3H, CH₃), 3.31 (s, 6H, CH₃), 7.11 (d, 1H, J=5.5 Hz, pyrimidinyl-H), 7.53 (m, 2H, Ph-H), 7.88 (m, 2H, Ph-H), 8.44 (d, 1H, J=5.5 Hz, pyrimidinyl-H), 8.68 (br. s, 1H, NH).

The following compounds was obtained in an analogous manner:

(4-Iodo-3-nitro-phenyl)-[4-(4-methyl-2-methylamino-thiazol-5-yl)-pyrimidin-2-yl]-amine [30]

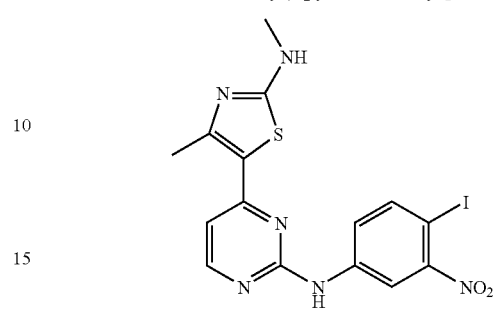

Dark-brown solid; ¹H-NMR (DMSO-d₆) δ: 2.49 (s, 3H, CH₃), 3.24 (s, 3H, CH₃), 6.96 (d, 1H, J=6.0 Hz, pyrimidinyl-H), 7.37 (d, 1H, J=8.0 Hz, Ph-H), 7.82 (m, 1H, Ph-H), 8.36 (d, 1H, J=6.0 Hz, pyrimidinyl-H), 8.68 (s, 1H, Ph-H), 9.86 (br. s, 1H, NH).

Example 9

5-[2-(4-Hydroxy-phenylamino)-pyrimidin-4-yl]-3,4-dimethyl-3H-thiazol-2-one [31]

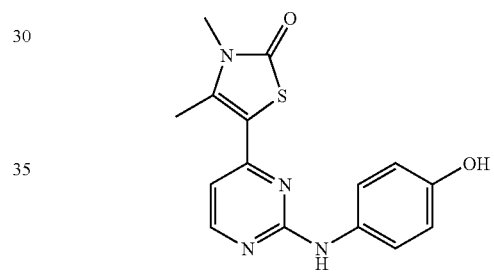

To an ice-cooled solution of potassium thiocyanate (5.67 g, 58 mmol) in Me₂CO (45 mL) was added 3-chloro-pentane-2,4-dione (6.95 mL, 58 mmol) dropwise. After completion of the addition the reaction mixture was warmed to room temperature and stirred for a further 6 h. The solvent was evaporated to dryness. The residue was dissolved in EtOH (30 mL) and HCl (conc. aq, 15 mL) was added. The mixture was heated to reflux for 14 h. It was concentrated and the precipitate was collected, washed with cold MeOH and then Et₂O to afford 9.1 g of a pale solid. This compound was treated with N,N-dimethylformamide dimethylacetal (13 mL) at 100-110° C. for 8 h. The reaction mixture was concentrated and the residue was purified by SiO₂ flash chromatography (EtOAc/PE) to afford 3-dimethylamino-1-(2-methoxy-4-methyl-thiazol-5-yl)-propenone as a yellow solid. ¹H-NMR (CDCl₃) δ: 2.50 (s, 3H, CH₃), 3.07 (s, 3H, CH₃), 3.21 (s, 6H, CH₃), 5.09 (d, 1H, J=12.0 Hz, CH), 7.59 (d, 1H, J=12.0 Hz, CH).

A solution of 3-dimethylamino-1-(2-methoxy-4-methyl-thiazol-5-yl)-propenone (0.23 g, 1.0 mmol) in of 2-methoxy-ethanol (3 mL) was treated with N-(4-hydroxy-phenyl)-guanidine nitrate (0.42 g, 2.0 mmol). After refluxing for 20 h the reaction mixture was concentrated and purified by SiO₂ flash chromatography (EtOAc). Recrystallisation from EtOAc afforded the tilted compound (25 mg) as brown crystals. Anal. RP-HPLC: t_R=11.8 min (0-60% MeCN in 0.1% aq CF₃COOH over 20 min, 1 mL/min, purity >95%). ¹H-NMR (DMSO-d$_6$) δ: 2.52 (s, 3H, CH$_3$), 3.27 (s, 3H, CH$_3$), 6.68 (d, 2H, J=8.9 Hz, Ph-H), 6.81 (d, 1H, J=5.5 Hz, pyrimidinyl-H), 7.44 (d, 2H, J=8.9 Hz, Ph-H), 8.34 (d, 1H, J=5.5 Hz, pyrimidinyl-H), 9.12 (br. s, 1H, OH/NH), 9.24 (br. s, 1H, NH/OH).

Example 10

The following compounds were prepared in a similar manner to the procedures described above:

3,4-Dimethyl-5-[2-(3-nitro-phenylamino)-pyrimidin-4-yl]-3H-thiazol-2-one [32]

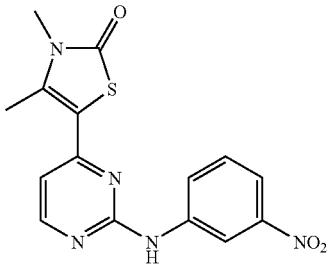

Brown crystals. Anal. RP-HPLC: t$_R$=17.8 min (0-60% MeCN in 0.1% aq CF$_3$COOH over 20 min, 1 mL/min, purity >97%). $^1$H-NMR (DMSO-d$_6$) δ: 2.42 (s, 3H, CH$_3$), 3.16 (s, 3H, CH$_3$), 6.92 (d, 1H, J=5.0 Hz, pyrimidinyl-H), 7.42 (d, 1H, J=8.0 Hz, Ph-H) 7.65 (m, 1H, Ph-H), 7.88 (m, 1H, Ph-H), 8.37 (d, 1H, J=5.0 Hz, pyrimidinyl-H), 8.72 (br. s, 1H, NH).

5-[2-(4-Iodo-phenylamino)-pyrimidin-4-yl]-3,4-dimethyl-3H-thiazol-2-one [33]

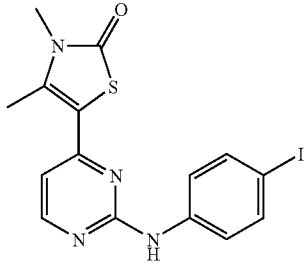

Brown solid; anal. RP-HPLC: t$_R$=18.8 min (0-60% MeCN in 0.1% aq CF$_3$COOH over 20 min, 1 mL/min, purity >95%). $^1$H-NMR (DMSO-d$_6$) δ: 2.83 (s, 3H, CH$_3$), 3.59 (s, 3H, CH$_3$), 7.24 (d, 1H, J=5.0 Hz, pyrimidinyl-H), 7.87 (m, 4H, Ph-H), 8.71 (d, 1H, J=5.0 Hz, pyrimidinyl-H). $^{13}$C-NMR (DMSO-d$_6$) δ: 14.96, 30.30, 85.01, 109.42, 109.41, 110.32, 121.93, 137.69, 137.70, 138.74, 140.89, 158.55, 159.24, 159.93, 170.39.

5-[2-(4-Fluoro-phenylamino)-pyrimidin-4-yl]-3,4-dimethyl-3H-thiazol-2-one [34]

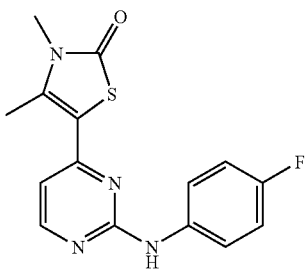

Gray solid; $^1$H-NMR (DMSO-d$_6$) δ: 2.92 (s, 3H, CH$_3$), 3.67 (s, 3H, CH$_3$), 7.32 (d, 1H, J=5.0 Hz, pyrimidinyl-H), 7.51 (m, 2H, Ph-H), 8.11 (m, 2H, Ph-H), 8.80 (d, 1H, J=5.0 Hz, pyrimidinyl-H).

5-[2-(4-Chloro-phenylamino)-pyrimidin-4-yl]-3,4-dimethyl-3H-thiazol-2-one [35]

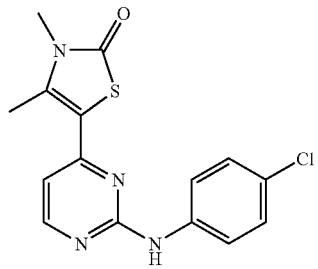

Light yellow solid; $^1$H-NMR (DMSO-d$_6$) δ: 2.55 (s, 3H, CH$_3$), 3.29 (s, 3H, CH$_3$), 6.97 (d, 1H, J=5.0 Hz, pyrimidinyl-H), 7.32 (d, 2H, J=8.5 Hz, Ph-H), 7.76 (d, 2H, J=9.0 Hz, Ph-H), 8.44 (d, 1H, J=5.0 Hz, pyrimidinyl-H), 9.75 (br. s, 1H, NH).

5-[2-(4-Methoxy-phenylamino)-pyrimidin-4-yl]-3,4-dimethyl-3H-thiazol-2-one [36]

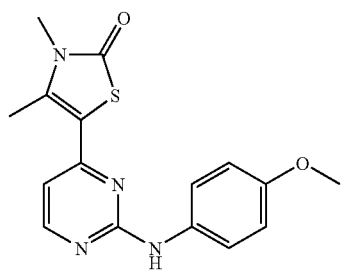

Light yellow solid; $^1$H-NMR (DMSO-d$_6$) δ: 2.54 (s, 3H, CH$_3$), 3.28 (s, 3H, CH$_3$), 3.71 (s, 3H, CH$_3$), 6.86 (m, 3H, pyrimidinyl-H & Ph-H), 7.59 (d, 2H, J=9.0 Hz, Ph-H), 8.37 (d, 1H, J=5.0 Hz, pyrimidinyl-H), 9.39 (br. s, 1H, NH).

5-[2-(3-Hydroxy-phenylamino)-pyrimidin-4-yl]-3,4-dimethyl-3H-thiazol-2-one [37]

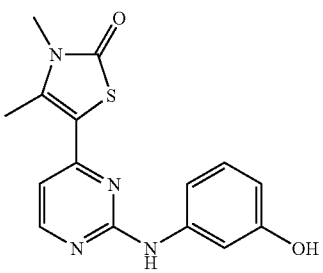

Light yellow solid; anal. RP-HPLC: t$_R$=15.4 min (0-60% MeCN in 0.1% aq VF$_3$COOH over 20 min, 1 mL/min, purity >95%). $^1$H-NMR (DMSO-d$_6$) δ: 2.55 (s, 3H, CH$_3$), 3.26 (s, 3H, CH$_3$), 6.36 (m, 1H, Ph-H), 6.90 (d, 1H, J=5.5 Hz, pyrimidinyl-H), 7.03 (t, 1H, J=8.5 Hz, Ph-H), 7.16 (m, 1H, Ph-H), 7.22 (s, 1H, Ph-H), 8.40 (d, 1H, J=5.5 Hz, pyrimidinyl-H), 9.39 (br. s, 1H, NH).

5-[2-(4-Fluoro-3-nitro-phenylamino)-pyrimidin-4-yl]-3,4-dimethyl-3H-thiazol-2-one [38]

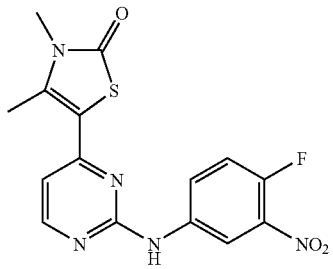

Brown solid; $^1$H-NMR (DMSO-d$_6$) δ: 2.42 (s, 3H, CH$_3$), 2.81 (s, 3H, CH$_3$), 6.36 (m, 1H, Ph-H), 6.91 (d, 1H, J=5.5 Hz, pyrimidinyl-H), 7.31 (m, 1H, Ph-H), 8.33 (m, 1H, Ph-H), 8.48 (d, 1H, J=5.5 Hz, pyrimidinyl-H), 8.52 & 9.68 (br. s, 1H, NH).

5-[2-(4-Chloro-3-methyl-phenylamino)-pyrimidin-4-yl]-3,4-dimethyl-3H-thiazol-2-one [39]

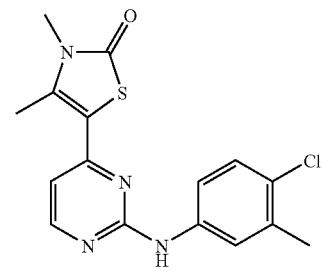

Yellow solid; $^1$H-NMR (DMSO-d$_6$) δ: 2.30 (s, 3H, CH$_3$), 2.55 (s, 3H, CH$_3$), 3.27 (s, 3H, CH$_3$), 6.96 (d, 1H, J=5.5 Hz, pyrimidinyl-H), 7.30 (d, 1H, J=9.0 Hz, Ph-H), 7.52 (m, 1H, Ph-H), 7.81 (m, 1H, Ph-H), 8.43 (d, 1H, J=5.5 Hz, pyrimidinyl-H), 9.69 (br. s, 1H, NH).

5-[2-(3-Iodo-4-methyl-phenylamino)-pyrimidin-4-yl]-3,4-dimethyl-3H-thiazol-2-one [40]

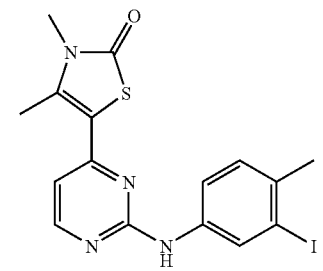

Brown solid; $^1$H-NMR (DMSO-d$_6$) δ: 2.28 (s, 3H, CH$_3$), 3.30 (s, 3H, CH$_3$), 6.96 (d, 1H, J=5.0 Hz, pyrimidinyl-H), 7.14 (m, 1H, Ph-H), 7.21 (m, 1H, Ph-H), 7.53 (m, 1H, Ph-H), 8.42 (d, 1H, J=5.0 Hz, pyrimidinyl-H), 9.65 (br. s, 1H, NH).

5-[2-(4-Fluoro-3-methyl-phenylamino)-pyrimidin-4-yl]-3,4-dimethyl-3H-thiazol-2-one [41]

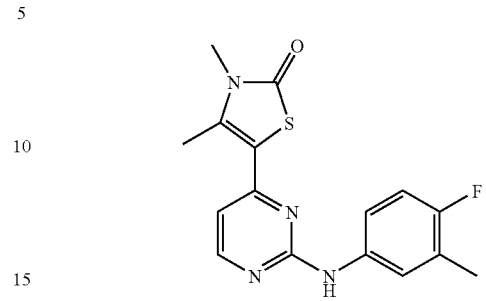

Grey solid; $^1$H-NMR (DMSO-d$_6$) δ: 2.21 (s, 3H, CH$_3$), 2.55 (s, 3H, CH$_3$), 3.26 (s, 3H, CH$_3$), 6.92 (d, 1H, J=5.0 Hz, pyrimidinyl-H), 7.04 (t, 1H, J=9.0 Hz, Ph-H), 7.48 (m, 1H, Ph-H), 7.68 (m, 1H, Ph-H), 8.40 (d, 1H, J=5.5 Hz, pyrimidinyl-H), 9.54 (br. s, 1H, NH).

3,4-Dimethyl-5-[2-(4-methyl-3-nitro-phenylamino)-pyrimidin-4-yl]-3H-thiazol-2-one [42]

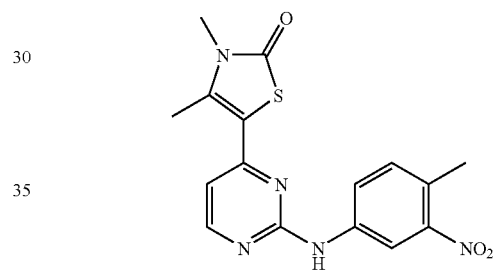

Yellow solid; $^1$H-NMR (DMSO-d$_6$) δ: 2.44 (s, 3H, CH$_3$), 2.55 (s, 3H, CH$_3$), 3.27 (s, 3H, CH$_3$), 7.03 (d, 1H, J=5.0 Hz, pyrimidinyl-H), 7.40 (t, 1H, J=8.5 Hz, Ph-H), 7.84 (m, 1H, Ph-H), 8.48 (d, 1H, J=5.0 Hz, pyrimidinyl-H), 8.59 (s, 1H, Ph-H), 9.99 (br. s, 1H, NH).

5-[2-(4-Dimethylamino-phenylamino)-pyrimidin-4-yl]-3,4-dimethyl-3H-thiazol-2-one [43]

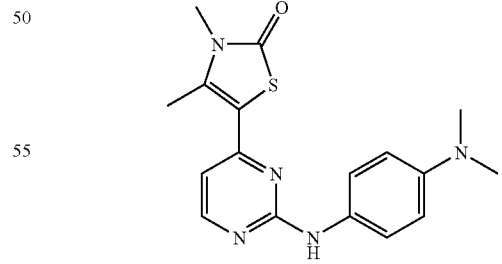

Yellow solid; anal. RP-HPLC: t$_R$=19.6 min (0-60% MeCN in 0.1% aq CF$_3$COOH over 20 min, 1 mL/min, purity >95%). $^1$H-NMR (DMSO-d$_6$) δ: 2.83 (s, 3H, CH$_3$), 2.90 (s, 6H, CH$_3$), 3.08 (s, 3H, CH$_3$), 6.73 (m, 2H, Ph-H), 6.81 (d, 1H, J=5.5 Hz, pyrimidinyl-H), 7.03 (m, 1H, Ph-H), 7.50 (m, 1H, Ph-H), 8.32 (d, 1H, J=5.5 Hz, pyrimidinyl-H), 9.24 (br. s, 1H, NH).

Example 11

[4-(2-Ethylamino-4-methyl-thiazol-5-yl)-pyrimidin-2-yl]-(3-nitro-phenyl)-amine [44]

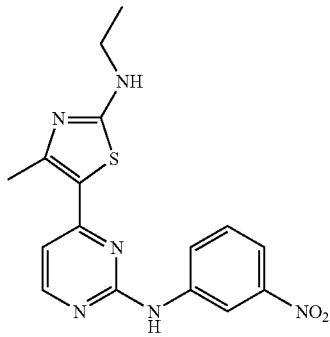

3-Dimethylamino-1-(2-ethylamino-4-methyl-thiazol-5-yl)-propenone was prepared by reaction between 1-(2-ethylamino-4-methyl-thiazol-5-yl)-ethanone and 3-chloro-pentane-2,4-dione. It was then condensed with N-(3-nitro-phenyl)-guanidine nitrate in the usual manner to afford the title compound. Yellow solid; $^1$H-NMR (DMSO-$d_6$) δ: 1.14 (m, 3H, CH$_3$), 2.47 (s, 3H, CH$_3$), 3.23 (m, 2H, CH$_2$), 6.99 (d, 1H, J=5.0 Hz, pyrimidinyl-H), 7.55 (m, 1H, Ph-H), 7.77 (m, 1H, Ph-H), 8.02 (m, 1H, Ph-H), 8.39 (d, 1H, J=5.0 Hz, pyrimidinyl-H), 8.47 (s, 1H, Ph-H), 9.98 (br. s, 1H, NH).

Example 12

The following compounds were prepared in a manner analogous to that described in Example 11 above:

(4-Chloro-phenyl)-[4-(2-ethylamino-4-methyl-thiazol-5-yl)-pyrimidin-2-yl]-amine [45]

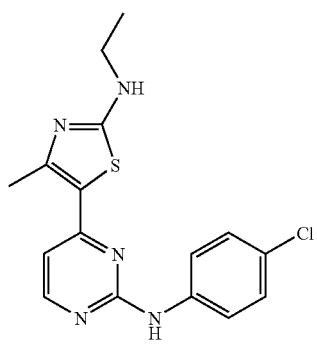

Brown solid; $^1$H-NMR (DMSO-$d_6$) δ: 1.16 (m, 3H, CH$_3$), 2.45 (s, 3H, CH$_3$), 3.24 (m, 2H, CH$_2$), 6.90 (d, 1H, J=5.0 Hz, pyrimidinyl-H), 7.30 (d, 2H, J=9.0 Hz, Ph-H), 7.79 (d, 2H, J=9.0 Hz, Ph-H), 8.32 (d, 1H, J=5.0 Hz, pyrimidinyl-H), 9.57 (sbr, 1H, NH).

[4-(2-Ethylamino-4-methyl-thiazol-5-yl)-pyrimidin-2-yl]-(4-trifluoromethyl-phenyl)-amine [47]

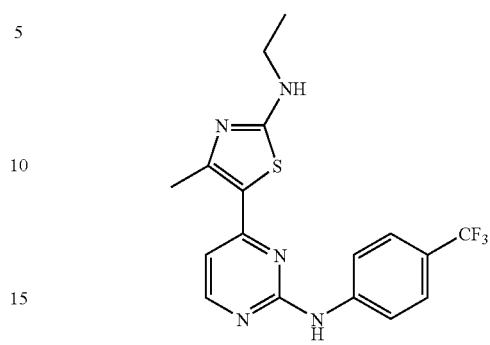

Brown solid; $^1$H-NMR (DMSO-$d_6$) δ: 1.16 (t, 3H, J=7.0 Hz, CH$_3$), 2.46 (s, 3H, CH$_3$), 3.27 (m, 2H, CH$_2$), 6.98 (d, 1H, J=5.5 Hz, pyrimidinyl-H), 7.60 (d, 2H, J=9.0 Hz, Ph-H), 7.97 (d, 2H, J=9.0 Hz, Ph-H), 8.14 (br. s, 1H, NH), 8.37 (d, 1H, J=5.5 Hz, pyrimidinyl-H), 9.86 (br. s, 1H, NH).

[4-(2-Ethylamino-4-methyl-thiazol-5-yl)-pyrimidin-2-yl]-(3-methoxy-phenyl)-amine [48]

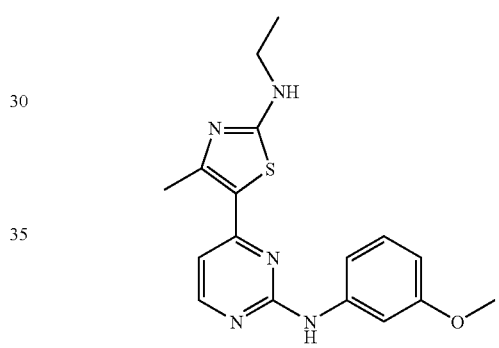

Brown solid; $^1$H-NMR (DMSO-$d_6$) δ: 1.17 (m, 3H, CH$_3$), 2.48 (s, 3H, CH$_3$), 3.25 (m, 2H, CH$_2$), 6.49 (m, 1H, Ph-H), 6.89 (d, 1H, J=5.5 Hz, pyrimidinyl-H), 7.14 (t, 1H, J=8.5 Hz, Ph-H), 7.26 (m, 1H, Ph-H), 7.52 (m, 1H, Ph-H), 8.31 (d, 1H, J=5.5 Hz, pyrimidinyl-H), 8.49 (br. s, 1H, NH), 9.39 (br. s, 1H, NH).

(3-Chloro-phenyl)-[4-(2-ethylamino-4-methyl-thiazol-5-yl)-pyrimidin-2-yl]-amine [49]

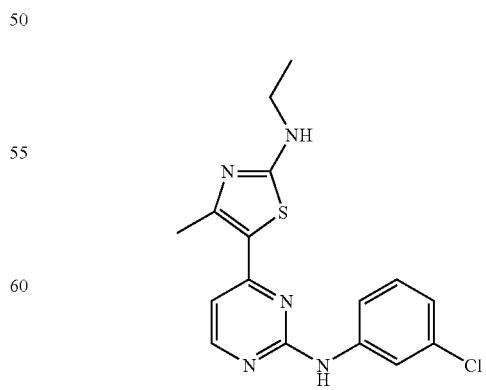

Brown solid; $^1$H-NMR (DMSO-$d_6$) δ: 1.15 (m, 3H, CH$_3$), 2.47 (s, 3H, CH$_3$), 3.22 (m, 2H, CH$_2$), 6.94 (m, 2H, Ph-H & pyrimidinyl-H), 7.26 (t, 1H, J=9.0 Hz, Ph-H), 7.58 (m, 1H, Ph-H), 8.10 (m, 1H, Ph-H), 8.35 (d, 1H, J=5.5 Hz, pyrimidinyl-H), 9.65 (br. s, 1H, NH).

[4-(2-Ethylamino-4-methyl-thiazol-5-yl)-pyrimidin-2-yl]-(4-methyl-3-nitro-phenyl)-amine [50]

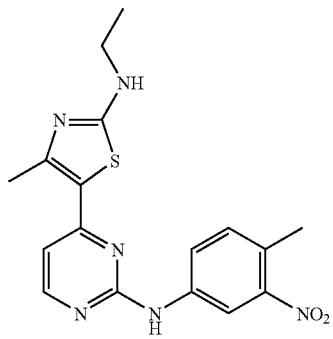

Brown solid; $^1$H-NMR (DMSO-$d_6$) δ: 1.19 (t, 3H, J=7.5 Hz, CH$_3$), 2.49 (s, 3H, CH$_3$), 3.24 (m, 2H, CH$_2$), 6.95 (d, 1H, J=5.5 Hz, pyrimidinyl-H), 7.37 (d, 1H, J=8.5 Hz, Ph-H), 7.81 (m, 1H, Ph-H), 8.35 (d, 1H, J=5.5 Hz, pyrimidinyl-H), 8.66 (s, 1H, Ph-H), 9.83 (br. s, 1H, NH).

Example 13

[4-(2-Butylamino-4-methyl-thiazol-5-yl)-pyrimidin-2-yl]-(4-fluoro-phenyl)-amine [51]

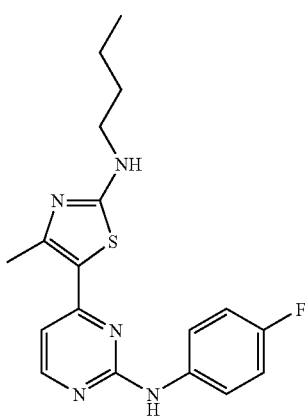

The titled compound was prepared by condensation of 1-(2-butylamino-4-methyl-thiazol-5-yl)-3-dimethylamino-propenone with 4-fluorophenylguanidine nitrate in the usual manner to afford the title compound. Grey solid; $^1$H-NMR (DMSO-$d_6$) δ: 0.90 (m, 3H, CH$_3$), 1.33 (m, 2H, CH$_2$), 1.53 (m, 2H, CH$_2$), 2.48 (s, 3H, CH$_3$), 3.22 (m, 2H, CH$_2$), 6.87 (d, 1H, J=5.0 Hz, pyrimidinyl-H), 7.10 (m, 2H, Ph-H), 7.74 (m, 2H, Ph-H), 8.11 (br. s, 1H, NH), 8.30 (d, 1H, J=5.5 Hz, pyrimidinyl-H), 9.42 (br. s, 1H, NH).

Example 14

[4-(2-Dimethylamino-4-methyl-thiazol-5-yl)-pyrimidin-2-yl]-(3-nitro-phenyl)-amine [52]

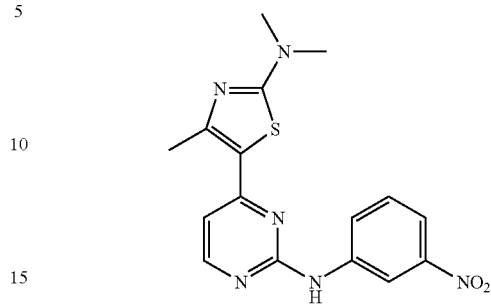

A mixture of 1-(4-methyl-2-methylamino-thiazol-5-yl)-ethanone (0.40 g, 2.4 mmol) in THF (2 mL) was treated with NaH (0.113 g, 4.7 mmol). After heating at 40° C. for 0.5 h MeI (0.35 g, 2.4 mmol) was added. Heating was continued for a further 2 h. After cooling, the solution was diluted with EtOAc, washed with brine, and dried over MgSO$_4$. The solvent was evaporated to afford 1-(2-dimethylamino-4-methyl-thiazol-5-yl)-ethanone as a yellow solid. $^1$H-NMR (CDCl$_3$) δ: 2.36 (s, 3H, CH$_3$), 2.51 (s, 3H, CH$_3$), 3.10 (s, 6H, CH$_3$).

The above compound was heated in of N,N-dimethylformamide dimethylacetal (2 mL) at 125° C. for 4 h. The reaction mixture was concentrated and the residue was purified by SiO$_2$ chromatography (EtOAc/MeOH, 95:5) to afford the desired product 3-dimethylamino-1-(2-dimethylamino-4-methyl-thiazol-5-yl)-propenone. $^1$H-NMR (CDCl$_3$) δ: 2.49 (s, 6H, CH$_3$), 3.03 (s, 6H, CH$_3$), 3.29 (s, 3H, CH$_3$), 5.23 (d, 1H, J=12.0 Hz, CH), 7.51 (d, 1H, J=12.0 Hz, CH). Condensation of this compound with N-(3-nitro-phenyl)-guanidine nitrate in the usual manner afforded the titled compound as a brown solid. $^1$H-NMR (DMSO-$d_6$) δ: 3.12 (s, 9H, CH$_3$), 7.02 (d, 1H, J=5.0 Hz, pyrimidinyl-H), 7.55 (t, 1H, J=8.0 Hz, Ph-H), 7.77 (m, 1H, Ph-H), 7.93 (m, 1H, Ph-H), 8.41 (d, 1H, J=6.0 Hz, pyrimidinyl-H), 8.49 (s, 1H, Ph-H), 9.10 (br. s, 1H, NH).

Example 15

The following compounds were prepared in a manner analogous to that described in Example 14 above:

(4-Chloro-phenyl)-[4-(2-dimethylamino-4-methyl-thiazol-5-yl)-pyrimidin-2-yl]-amine [53]

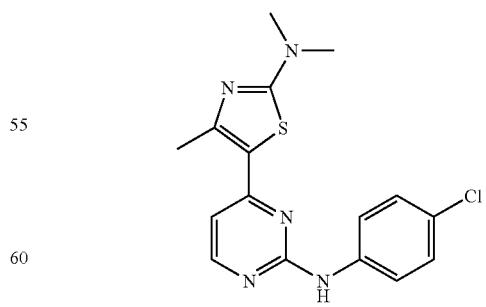

Brown solid; $^1$H-NMR (DMSO-$d_6$) δ: 3.09 (s, 9H, CH$_3$), 6.93 (d, 1H, J=5.5 Hz, pyrimidinyl-H), 7.32 (d, 2H, J=9.5 Hz, Ph-H), 7.79 (d, 2H, J=9.5 Hz, Ph-H), 8.33 (d, 1H, J=5.0 Hz, pyrimidinyl-H), 9.57 (br. s, 1H, NH).

[4-(2-Dimethylamino-4-methyl-thiazol-5-yl)-pyrimidin-2-yl]-(4-fluoro-phenyl)-amine [54]

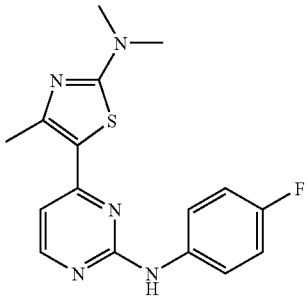

Grey solid; ¹H-NMR (DMSO-d₆) δ: 3.08 (s, 9H, CH₃), 6.89 (d, 1H, J=5.0 Hz, pyrimidinyl-H), 7.11 (m, 2H, Ph-H), 7.74 (m, 2H, Ph-H), 8.31 (d, 1H, J=5.5 Hz, pyrimidinyl-H), 9.44 (br. s, 1H, NH).

(3-Chloro-phenyl)-[4-(2-dimethylamino-4-methyl-thiazol-5-yl)-pyrimidin-2-yl]-amine [55]

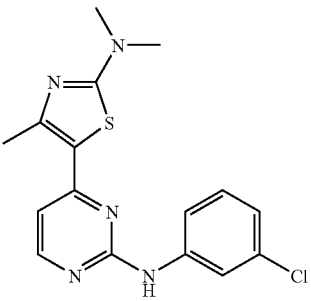

Brown solid; ¹H-NMR (DMSO-d₆) δ: 3.10 (s, 9H, CH₃), 6.96 (d, 2H, pyrimidinyl-H & Ph-H), 7.27 (t, 1H, J=8.0 Hz, Ph-H), 7.52 (m, 1H, Ph-H), 8.20 (s, 1H, Ph-H), 8.37 (d, 1H, J=5.5 Hz, pyrimidinyl-H), 9.71 (br. s, 1H, NH).

Example 16

N-{4-Methyl-5-[2-(3-nitro-phenylamino)-pyrimidin-4-yl]-thiazol-2-yl}-methane sulfonamide [56]

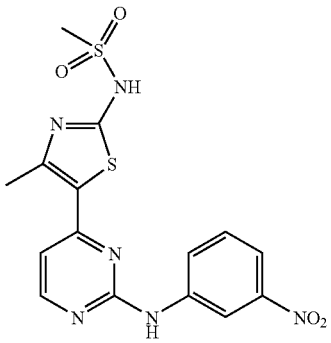

A mixture of [4-(2-amino-4-methyl-thiazol-5-yl)-pyrimidin-2-yl]-(3-nitro-phenyl)-amine (1.0 mmol, 0.33 g) and methylsulfonyl chloride (2.0 mmol, 0.22 g) in dry DMF (2 mL) was added Et₃N (0.28 mL). The reaction mixture was stirred at room temperature for 20 h. After cooling, the mixture was diluted with EtOAc, washed with brine, and dried over MgSO₄. The solvent was evaporated and the residue was purified by preparative RP-HPLC using a gradient from 10-70% MeCN in 0.1% aq CF₃COOH over 40 min. The title compound was obtained as an orange solid. Anal. RP-HPLC: t$_R$=17.4 min (0-60% MeCN in 0.1% aq CF₃COOH over 20 min, 1 mL/min, purity >97%). ¹H-NMR (DMSO-d₆) δ: 3.10 (s, 3H, CH₃), 3.25 (s, 3H, CH₃), 7.05 (d, 1H, J=5.2 Hz, pyrimidinyl-H), 7.42 (m, 1H, Ph-H), 7.63 (m, 1H, Ph-H), 7.98 (m, 1H, Ph-H), 8.21 (d, 1H, J=5.2 Hz, pyrimidinyl-H), 8.42 (s, 1H, Ph-H), 9.18 (s, 1H, NH).

Example 17

2-{4-Methyl-5-[2-(3-nitro-phenylamino)-pyrimidin-4-yl]-thiazol-2-ylamino}-ethanol [58]

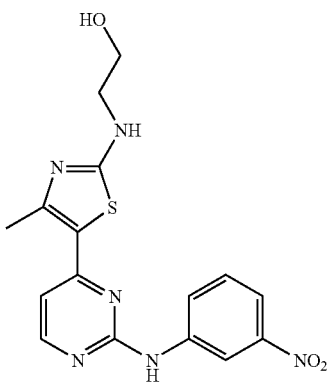

To a mixture of [4-(2-amino-4-methyl-thiazol-5-yl)-pyrimidin-2-yl]-(3-nitro-phenyl)-amine (0.33 g, 1.0 mmol) and iodoethanol (0.44 g, 2.6 mmol) in dry DMF (2 mL) was added tert-butylimino-2-diethylamino-1,3-dimethylperhydro-1,3-diazaphosphorine (0.5 mL). The reaction mixture was heated at 124° C. for 20 h. The product was isolated as a brown solid by preparative RP-HPLC (Vydac 218TP1022, 9 mL/min) using a gradient from 10-70% MeCN in 0.1% aq CF₃COOH over 40 min. Anal. RP-HPLC: t$_R$=14.30 min (Vydac 218TP54, 0-60% MeCN in 0.1% aq CF₃COOH over 20 min, 1 mL/min, 25° C., purity >97%). ¹H-NMR (CD₃OD) δ: 3.30 (s, 3H, CH₃), 3.91 (t, 2H, J=4.6 Hz, CH₂), 4.25 (t, 2H, J=4.6 Hz, CH₂), 7.21 (d, 1H, J=5.2 Hz, pyrimidinyl-H), 7.54 (m, 1H, Ph-H), 7.89 (m, 2H, Ph-H), 8.59 (d, 1H, J=5.2 Hz, pyrimidinyl-H), 8.90 (s, 1H, Ph-H).

2-{5-[2-(4-Fluoro-phenylamino)-pyrimidin-4-yl]-4-methyl-thiazol-2-ylamino}-ethanol [59]

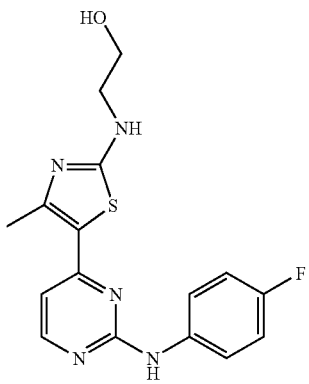

This compound was prepared from [4-(2-amino-4-methyl-thiazol-5-yl)-pyrimidin-2-yl]-(4-fluoro-phenyl)-amine in a manner analogous to that described for compound [58]. $^1$H-NMR (DMSO-$d_6$) δ: 2.44 (s, 3H, CH$_3$), 3.54 (m, 2H, CH$_2$), 4.78 (m, 2H, CH$_2$), 6.87 (d, 1H, J=5.2 Hz, pyrimidinyl-H), 7.09 (m, 2H, Ph-H), 7.75 (m, 2H, Ph-H), 8.30 (d, 1H, J=5.2 Hz, pyrimidinyl-H), 8.11 (m, 1H, NH), 9.43 (s, 1H, NH). DE MALDI-TOF MS: [M+H]$^+$=345.79 (C$_{16}$H$_{16}$FN$_5$OS requires 345.40).

Example 18

2-Chloro-N-{4-methyl-5-[2-(3-nitro-phenylamino)-pyrimidin-4-yl]-thiazol-2-yl}-acetamide [60]

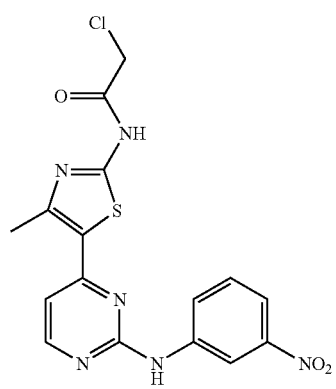

A solution of [4-(2-amino-4-methyl-thiazol-5-yl)-pyrimidin-2-yl]-(3-nitro-phenyl)-amine (0.33 g, 1.0 mmol) in dry DMF (3 mL) was cooled on an ice-water bath. Chloroacetyl chloride (0.22 g, 2.0 mmol) and pyridine (80 µL) were added. After stirring at room temperature for 18 h, the product was isolated as a brown solid by preparative RP-HPLC (Vydac 218TP1022, 9 mL/min) using a gradient from 10-70% MeCN in 0.1% aq CF$_3$COOH over 40 min. Anal. RP-HPLC: $t_R$=20.62 min (Vydac 218TP54, 0-60% MeCN in 0.1% aq CF$_3$COOH over 20 min, 1 mL/min, 25° C., purity >97%). $^1$H-NMR (DMSO-$d_6$) δ: 2.45 (s, 3H, CH$_3$), 4.12 (s, 2H, CH$_2$), 7.03 (d, 1H, J=5.2 Hz, pyrimidinyl-H), 7.42 (m, 1H, Ph-H), 7.63 (m, 1H, Ph-H), 8.01 (m, 1H, Ph-H), 8.41 (d, 1H, J=5.2 Hz, pyrimidinyl-H), 8.64 (s, 1H, Ph-H).

The following compounds were prepared in an analogous manner:

2-Chloro-N-{5-[2-(4-fluoro-phenylamino)-pyrimidin-4-yl]-4-methyl-thiazol-2-yl}-acetamide [61]

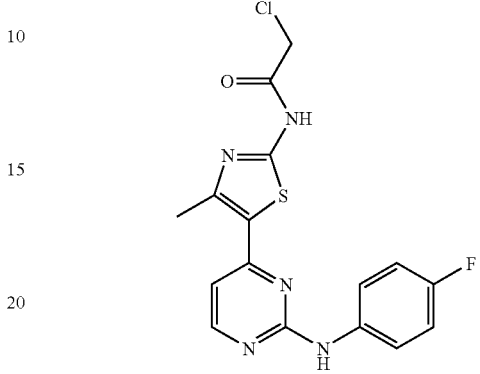

This compound was prepared from [4-(2-amino-4-methyl-thiazol-5-yl)-pyrimidin-2-yl]-(4-fluoro-phenyl)-amine in a manner analogous to that described above for compound [60]. $^1$H-NMR (DMSO-$d_6$) δ: 2.94 (s, 3H, CH$_3$), 4.75 (s, 2H, CH$_2$), 7.44(m, 3H, pyrimidinyl-H & Ph-H), 8.09 (m, 2H, Ph-H), 8.28 (s, 1H, NH), 8.80 (d, 1H, J=5.2 Hz, pyrimidinyl-H).

The biological activity of the compounds of the invention was demonstrated by measuring the CDK inhibition by virtue of an assay-based screen, and/or by a cytotoxicity assay using one or more cell lines (see Table 1).

Example 19

Kinase Specificity of Selected Compound

The compounds from the examples above were investigated for their ability to inhibit the enzymatic activity of various protein kinases. In particular, CDK2/cyclin E and CDK4/cyclin D1 were assayed.

Kinase assays were performed in 96-well plates using recombinant proteins and appropriate assay buffers (typically 25 mM β-glycerophosphate, 20 mM MOPS, 5 mM EGTA, 1 mM DTT, 1 mM Na$_3$VO$_3$, pH 7.4), into which were added 2-4 µg of active enzyme with appropriate substrates (purified histone H1 for CDK2, recombinant GST-retinoblastoma protein (residues 773-928) for CDK4). The reactions were initiated by addition of Mg/ATP mix (15 mM MgCl$_2$+100 µM ATP with 30-50 kBq per well of [γ-$^{32}$P]-ATP) and mixtures incubated for 10 min (CDK2/cyclin E) or 45 min (CDK4/cyclin D1) as required, at 30° C. Reactions were stopped on ice, followed by filtration through p81 filterplates or GF/C filterplates (for CDK4) (Whatman Polyfiltronics, Kent, UK. After washing 3 times with 75 mM aq orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (GraphPad Prism version 3.00 for Windows, GraphPad Software, San Diego Calif. USA) to determine IC$_{50}$ values (concentration of test compound which inhibits kinase activity by 50%.).

Alternatively, assays for CDK4/Cyclin D1, CDK2/Cyclin E, CDIK1/Cyclin B kinase may be carried out by monitoring phosphorylation of GST-Rb in an appropriate system. Thus, GST-Rb phosphorylation, induced by CDK4/Cyclin D1, CDK2/Cyclin E or CDK1/Cyclin B is determined by incorporation of radio-labeled phosphate in GST-Rb(772-928) using radiolabelled ATP in 96-well format in vitro kinase assay. The phosphorylation reaction mixture (total volume 40 µl) consisted of 50 mM HEPES pH 7.4, 20 mM MgCl$_2$, 5 mM EGTA, 2 mM DTT, 20 mM β-glycerophosphate, 2 mM NaF, 1 mM Na$_3$VO$_4$, Protease Inhibitors Cocktail (Sigma, see above), BSA 0.5 mg/ml, 1 µg purified enzyme complex, 10 µl of GST-Rb-Sepharose beads, 100 µM ATP, 0.2 µCi $^{32}$P-ATP. The reaction is carried out for 30 min at 30° C. at constant shaking. At the end of this period 100 µl of 50 mM HEPES, pH 7.4 and 1 mM ATP is added to each well and the total volume transferred onto GFC filtered plate. The plate is washed 5 times with 200 µl of 50 mM HEPES, pH 7.4 and 1 mM ATP. To each well were added 50 µl scintillant liquid and the radioactivity of the samples is measured on Scintilation counter (Topcount, HP). The IC50 values of different peptides were calculated using GraFit software.

PKCα kinase activity may be measured by the incorporation of radio-labeled phosphate in Histone 3, as described. The reaction mixture (total volume 65 µl) consist of 50 mM Tris-HCl, 1 mM Calcium acetate, 3 mM DTT, 0.03 mg/ml Phosphatidylserine, 2.4 µg/ml PMA, 0.04% NP40, 12 mM Mg/Cl, purified PKCα-100 ng, Histone 3, 0.2 mg/ml, 100 µM ATP, 0.2 µCi [γ-$^{32}$P]-ATP. The reaction is carried over 15 min at 37° C. in microplate shaker and is stopped by adding 10 µl 75 mM orthophosphoric acid and placing the plate on ice. 50 µl of the reaction mixture is transferred onto P81 filterplate and after washing off the free radioactive phosphate (3 times with 200 µl 75 mM orthophosphoric acid per well) 50 µl of scintillation liquid (Microscint 40) were added to each well and the radioactivity is measured on Scintillation counter (Topcount, HP).

For use in said assays CDK2, CDK4 and/or PKC may be obtained from available sources or produced by recombinant methods as described. His$_6$-tagged recombinant human CDK2/cyclin E, CDK1/Cyclin B, CDK4 and PKCα can be expressed in Sf 9 insect cells infected with the appropriate baculovirus constructs. The cells are harvested two days after infection by low speed centrifugation and the proteins purified from the insect cell pellets by metal-chelate chromatography (to greater than 90% homogeneity). Briefly, the insect cell pellet is lysed in Buffer A (10 mM Tris-HCl, pH 8.0, 150 mM NaCl, 0.02% NP40 and 5 mM β-marcaptoethanol, 1 mM NaF. 1 mM Na$_3$VO$_4$ and Protease Inhibitors Coctail (Sigma) containing AEBSF, pepstatin A, E 64, bestatin, leupeptin) by sonication. The soluble fraction is cleared by centrifugation and loaded onto Ni-NTA-Agarose (Quiagen). Non bound proteins were washed off with 300 mM NaCl, 5-15 mM Imidazole in Buffer A and the bound proteins eluted with 250 mM Imidazole in Buffer A. The purified proteins are extensively dialyzed against Storage buffer (20 mM HEPES pH 7.4, 50 mM NaCl, 2 mM DTT, 1 mM EDTA, 1 mM EGTA, 0.02% NP40, 10% v/v Glycerol) aliquoted and stored at −70° C. PKC-α-6×His may be purified the same way but using different buffers-50 mM NaH2PO4, pH 8.0 and 0.05% Triton X-100 instead of Tris and NP40 respectively.

The results in the Table 2 below show that the compounds in question exhibit a high degree of selectivity for inhibition of CDKs.

Example 20

MTT Cytotoxicity Assay

The compounds from the examples above were subjected to a standard cellular proliferation assay using human tumour cell lines obtained from the ATCC (American Type Culture Collection, 10801 University Boulevard, Manessas, Va. 20110-2209, USA). Standard 72-h MTT (thiazolyl blue; 3-[4,5-dimethylthiazol-2-yl]-2,5-diphenyltetrazolium bromide) assays were performed (Haselsberger, K.; Peterson, D. C.; Thomas, D. G.; Darling, J. L. Anti Cancer Drugs 1996, 7, 331-8; Loveland, B. E.; Johns, T. G.; Mackay, I. R.; Vaillant, F.; Wang, Z. X.; Hertzog, P. J. Biochemistry International 1992, 27, 501-10). In short: cells were seeded into 96-well plates according to doubling time and incubated overnight at 37° C. Test compounds were made up in DMSO and a 1/3 dilution series prepared in 100 µL cell media, added to cells (in triplicates) and incubated for 72 ho at 37° C. MTT was made up as a stock of 5 mg/mL in cell media and filter-sterilised. Media was removed from cells followed by a wash with 200 µL PBS. MTT solution was then added at 20 µL per well and incubated in the dark at 37° C. for 4 h. MTT solution was removed and cells again washed with 200 µL PBS. MTT dye was solubilised with 200 µL per well of DMSO with agitation. Absorbance was read at 540 nm and data analysed using curve-fitting software (GraphPad Prism version 3.00 for Windows, GraphPad Software, San Diego Calif. USA) to determine IC$_{50}$ values (concentration of test compound which inhibits cell growth by 50%).

The results in Table 3 below illustrate the anti-proliferative effect of compounds described in this application.

Various modifications and variations of the described methods of the invention will be apparent to those skilled in the art without departing from the scope and spirit of the invention. Modifications of the described modes for carrying out the invention which are obvious to those skilled in the relevant are, or related fields, are thus intended to fall within the scope of the following claims.

TABLE 1

Biological activity of selected compounds

| Compound | Kinase inhibition, IC$_{50}$ (µM) | | 72-h MTT in vitro IC$_{50}$ (µM) | | |
|---|---|---|---|---|---|
| | CDK2/E | CDK4/D1 | A549 | HT29 | Saos-2 |
| 1 | 0.0002 | 0.41 | 0.22 | 0.34 | 0.42 |
| 2 | 0.81 | 1.73 | 2.37 | 2.88 | 1.54 |
| 3 | 0.43 | 0.46 | 2.94 | 4.01 | 2.61 |
| 7 | 0.68 | 5.83 | 1.03 | 1.26 | 0.65 |
| 8 | 0.34 | 0.42 | 1.55 | 2.71 | 1.32 |
| 9 | 0.02 | 0.07 | 0.55 | 0.79 | 0.43 |
| 10 | 0.05 | 0.24 | 0.29 | 0.51 | 0.58 |
| 13 | 0.04 | 0.45 | 0.95 | 2.87 | 0.52 |
| 14 | 0.20 | 0.64 | 0.29 | 0.28 | 0.31 |
| 15 | 0.43 | 1.36 | 3.04 | 3.80 | 2.84 |
| 16 | 0.09 | 1.77 | 0.82 | 0.66 | 0.81 |
| 21 | 0.47 | 3.28 | 2.79 | 3.61 | 4.37 |
| 23 | 0.03 | 1.06 | 1.57 | 1.17 | 2.02 |
| 24 | 0.14 | 1.68 | 0.44 | 5.47 | 0.16 |
| 25 | 0.04 | 0.50 | 0.43 | 0.30 | 0.35 |
| 26 | 0.00 | 0.96 | 0.29 | 0.15 | 0.32 |
| 28 | 0.56 | 2.88 | 2.07 | 2.23 | 1.59 |
| 29 | 0.32 | 0.99 | 0.40 | 0.60 | 0.80 |
| 30 | 0.12 | 0.25 | 0.94 | 1.07 | 2.31 |
| 31 | 0.05 | 0.60 | 0.29 | 0.87 | 0.40 |
| 32 | 0.06 | 0.23 | 0.01 | 0.01 | 0.10 |
| 34 | 0.12 | 1.12 | 0.51 | 0.38 | 1.27 |
| 35 | 0.11 | 1.09 | 0.89 | 0.40 | 2.78 |
| 36 | 0.25 | 0.96 | 0.68 | 0.69 | 3.53 |

TABLE 1-continued

Biological activity of selected compounds

| Compound | Kinase inhibition, IC$_{50}$ (µM) | | 72-h MTT in vitro IC$_{50}$ (µM) | | |
|---|---|---|---|---|---|
| | CDK2/E | CDK4/D1 | A549 | HT29 | Saos-2 |
| 37 | 0.12 | 1.41 | 0.66 | 1.99 | 0.98 |
| 38 | 0.12 | 2.33 | 1.12 | 0.55 | 2.17 |
| 39 | 1.18 | 17.90 | nd | nd | nd |
| 40 | 0.70 | 3.98 | 6.63 | 7.74 | 22.00 |
| 41 | 0.13 | nt | 2.41 | 2.19 | 7.98 |
| 42 | 0.11 | nt | 0.003 | 0.004 | 0.005 |
| 43 | 0.75 | 3.82 | 2.20 | 1.69 | 3.36 |
| 52 | 0.12 | 10.04 | 2.47 | 3.41 | 2.57 |
| 56 | 0.01 | 1.13 | 0.10 | 0.17 | 0.16 |
| 58 | 0.004 | 0.11 | 0.01 | 0.09 | 0.06 |
| 59 | 0.08 | 15.04 | | | |
| 60 | 0.07 | 0.86 | 0.15 | 0.25 | 0.21 |
| 61 | 0.23 | 0.68 | 0.33 | 0.11 | 0.30 |

TABLE 2

Kinase specificity of selected compounds (IC$_{50}$, µM)

| | Compound | |
|---|---|---|
| Kinase | 25 | 26 |
| CDK2/E[1] | 0.04 | <0.02 |
| CDK2/A[2] | 0.1 | 0.6 |
| CDK1/B1[3] | 0.12 | 0.6 |
| CDK4/D1[4] | 0.5 | 1.0 |
| CDK7/H[5] | 1.3 | 4.8 |
| ERK-2[6] | >100 | 20 |
| PKCα[7] | >100 | 24 |
| Abl[8] | 9.9 | 1.6 |
| CK2[9] | 86 | 6.9 |
| Akt/PKB[10] | 61 | 6.3 |
| p70-S6K[11] | 25 | 32 |
| SAPK2a[12] | >100 | 86 |
| Cam-KII[13] | >100 | 69 |
| Plk1[14] | >100 | >100 |
| PKA[15] | >50 | 18 |
| GSK3β[16] | 0.9 | 2.2 |

[1]CDK2-cyclin E complex;
[2]CDK2-cyclin A complex;
[3]CDK1-cyclin B1 complex;
[4]CDK4-cyclin D1 complex;
[5]CDK7-cyclin H-MAT 1 complex;
[6]extracellular-signal-regulated kinase 2;
[7]protein kinase C α;
[8]Ableson tyrosine kinase;
[9]casein kinase 2;
[10]protein kinase B;
[11]p70 ribosomal protein S6 kinase;
[12]stress-activated protein kinase 2a;
[13]calmodulin-dependent protein kinase II;
[14]polo-like kinase 1;
[15]cAMP-dependent protein kinase;
[16]glycogen synthase kinase 3β.

TABLE 3

In vitro antiproliferative activity of selected compounds (72-h MTT IC$_{50}$, µM)

| Cell line | | Compound | | |
|---|---|---|---|---|
| Type | Designation | 10 | 15 | 16 |
| Bone osteosarcoma | Saos-2 | 0.43 | 0.93 | 0.73 |
| Bone osteosarcoma | U2OS | 0.50 | | |
| Breast | MCF-7 | 0.19 | 4.74 | |
| Cervix | Hela | 0.14 | 0.55 | 0.56 |
| Colon | HT29 | 0.10 | 0.41 | 0.25 |
| Colon | Lovo | 0.13 | 0.23 | 0.21 |
| Colon | H1299 | 0.27 | 0.63 | 1.06 |
| Colon | HCT-116 | 0.28 | 0.69 | 0.96 |
| Gastric adenocarcinoma | AGS | 0.30 | 1.05 | 1.11 |
| Leiomyosarcoma | SKUT-1B | 0.04 | 0.39 | 0.30 |
| Leiomyosarcoma | SKUT-1 | 0.30 | 0.81 | 0.64 |
| Chronic myelogenous leukaemia | K562 | 0.15 | 1.35 | 0.54 |
| Leukaemia | CCRF-CEM | 0.26 | 0.85 | 0.50 |
| Promyelocytic leukaemia | HL60 | 0.07 | 2.87 | 0.43 |
| Lung | nci-H460 | 0.18 | 0.60 | 0.28 |
| Lung | A549 | 0.60 | 0.95 | 1.32 |
| Neuroblastoma | SK-N-MC | 0.28 | 0.58 | 0.42 |
| Osteogenic sarcoma | SJSA-1 | 0.85 | 1.50 | |
| Prostate | DU-145 | 0.75 | 0.98 | 1.75 |
| Skin keratinocytes | Hacat | 0.17 | 0.73 | 0.50 |
| Uterine | Messa | 0.11 | 0.55 | 0.59 |
| Uterine | Messa-Dx5 | 0.13 | 0.14 | 0.59 |
| Foreskin fibroblast (non-transformed) | Hs27 | >5.0 | >5.0 | >5.0 |
| Foetal lung fibroblast (non-transformed) | IMR-90 | >5.0 | >5.0 | >5.0 |
| Foetal lung (non-transformed) | WI38 | >5.0 | >5.0 | >5.0 |
| Mean IC$_{50}$ for tumour cells | | 0.28 | 1.03 | 0.68 |

The invention claimed is:

1. A compound selected from the group consisting of:

5-[2-(4-Hydroxy-phenylamino)-pyrimidin-4-yl]-3,4-dimethyl-3H-thiazol-2-one [31];

3,4-Dimethyl-5-[2-(3-nitro-phenylamino)-pyrimidin-4-yl]-3H-thiazol-2-one [32];

5-[2-(4-Iodo-phenylamino)-pyrimidin-4-yl]-3,4-dimethyl-3H-thiazol-2-one [33];

5-[2-(4-Fluoro-phenylamino)-pyrimidin-4-yl]-3,4-dimethyl-3H-thiazol-2-one [34];

5-[2-(4-Chloro-phenylamino)-pyrimidin-4-yl]-3,4-dimethyl-3H-thiazol-2-one [35];

5-[2-(4-Methoxy-phenylamino)-pyrimidin-4-yl]-3,4-dimethyl-3H-thiazol-2-one [36];

5-[2-(3-Hydroxy-phenylamino)-pyrimidin-4-yl]-3,4-dimethyl-3H-thiazol-2-one [37];

5-[2-(4-Fluoro-3-nitro-phenylamino)-pyrimidin-4-yl]-3,4-dimethyl-3H-thiazol-2-one [38];

5-[2-(4-Chloro-3-methyl-phenylamino)-pyrimidin-4-yl]-3,4-dimethyl-3H-thiazol-2-one [39];

5-[2-(3-Iodo-4-methyl-phenylamino)-pyrimidin-4-yl]-3,4-dimethyl-3H-thiazol-2-one [40];

5-[2-(4-Fluoro-3-methyl-phenylamino)-pyrimidin-4-yl]-3,4-dimethyl-3H-thiazol-2-one [41];

3,4-Dimethyl-5-[2-(4-methyl-3-nitro-phenylamino)-pyrimidin-4-yl]-3H-thiazol-2-one [42]; and 5-[2-(4-Dimethylamino-phenylamino)-pyrimidin-4-yl]-3,4-dimethyl-3H-thiazol-2-one [43]; or a pharmaceutically acceptable salt thereof.

2. A compound according to claim 1, selected from the group consisting of:

5-[2-(4-Hydroxy-phenylamino)-pyrimidin-4-yl]-3,4-dimethyl-3H-thiazol-2-one [31];

3,4-Dimethyl-5-[2-(3-nitro-phenylamino)-pyrimidin-4-yl]-3H-thiazol-2-one [32];

5-[2-(4-Fluoro-phenylamino)-pyrimidin-4-yl]-3,4-dimethyl-3H-thiazol-2-one [34]; and 3,4-Dimethyl-5-[2-(4-methyl-3-nitro-phenylamino)-pyrimidin-4-yl]-3H-thiazol-2-one [42]; or a pharmaceutically acceptable salt thereof.

3. A compound according to claim 2, selected from the group consisting of:

5-[2-(4-Fluoro-phenylamino)-pyrimidin-4-yl]-3,4-dimethyl-3H-thiazol-2-one [34]; and 3,4-Dimethyl-5-[2-(4-methyl-3-nitro-phenylamino)-pyrimidin-4-yl]-3H-thiazol-2-one [42]; or a pharmaceutically acceptable salt thereof.

4. A compound according to claim 2, selected from the following:

5-[2-(4-Hydroxy-phenylamino)-pyrimidin-4-yl]-3,4-dimethyl-3H-thiazol-2-one [31]; and 3,4-Dimethyl-5-[2-(3-nitro-phenylamino)-pyrimidin-4-yl]-3H-thiazol-2-one [32]; or a pharmaceutically acceptable salt thereof.

5. The compound of claim 4, wherein said compound is 3,4-Dimethyl-5-[2-(3-nitro-phenylamino)-pyrimidin-4-yl]-3H-thiazol-2-one [32]or a pharmaceutically acceptable salt thereof.

6. A pharmaceutical composition comprising a compound according to claim 1, or a pharmaceutically acceptable salt thereof; together with a pharmaceutically acceptable diluent, excipient or carrier.

7. A pharmaceutical composition according to claim 6 which further comprises one or more other anticancer agents.

8. A method for treating a proliferative disorder in a subject, comprising administering one or more compound of claim 1, or a pharmaceutically acceptable salt thereof, to a subject, such that the subject is treated for said proliferative disorder, wherein said proliferative disorder is selected from the group consisting of bone cancer, breast cancer, cervical cancer, colon cancer, stomach cancer, leiomyosarcoma, leukemia, lung cancer, brain cancer, prostate cancer, skin cancer and uterine cancer.

9. The method of claim 8, wherein the subject is treated for leukemia.

10. The method of claim 8, wherein said one or more compounds are administered in an amount sufficient to inhibit at least one CDK enzyme.

11. The method of claim 10 wherein the CDK enzyme is CDK2 or CDK4.

12. The method of claim 8, wherein said compound is administered in combination with one or more other anticancer agents.

13. The method of claim 8, wherein said proliferative disorder is lung cancer.

14. The method of claim 8, wherein said proliferative disorder is colon cancer.

15. The method of claim 8, wherein said proliferative disorder is bone cancer.

16. The method of claim 15, wherein said bone cancer is bone osteosarcoma or osteogenic sarcoma.

17. The method of claim 8, wherein said proliferative disorder is breast cancer.

18. The method of claim 8, wherein said proliferative disorder is cervical cancer.

19. The method of claim 8, wherein said stomach cancer is gastric adenocarcinoma.

20. The method of claim 8, wherein said proliferative disorder is leiomyosarcoma.

21. The method of claim 9, wherein said leukemia is chronic myelogenous leukemia or promyelocytic leukemia.

22. The method of claim 8, wherein said brain cancer is neuroblastoma.

23. The method of claim 8, wherein said proliferative disorder is prostate cancer.

24. The method of claim 8, wherein said proliferative disorder is skin cancer.

25. The method of claim 8, wherein said proliferative disorder is uterine cancer.

* * * * *